(12) United States Patent
Rosheim

(10) Patent No.: US 6,658,962 B1
(45) Date of Patent: Dec. 9, 2003

(54) ROBOTIC MANIPULATOR

(75) Inventor: Mark E. Rosheim, St. Paul, MN (US)

(73) Assignee: Ross-Hime Designs, Incorporated, Minneapolis, MN (US)

( * ) Notice: Subject to any disclaimer, the term of this patent is extended or adjusted under 35 U.S.C. 154(b) by 0 days.

(21) Appl. No.: 10/284,926

(22) Filed: Oct. 31, 2002

Related U.S. Application Data

(60) Provisional application No. 60/336,477, filed on Oct. 31, 2001.

(51) Int. Cl.[7] .................................................. B25J 17/02
(52) U.S. Cl. ........................ 74/490.05; 901/16; 901/26; 901/28
(58) Field of Search .................... 74/490.01, 490.03, 74/490.05, 490.06; 901/15, 16, 23, 25, 26, 28

(56) References Cited

U.S. PATENT DOCUMENTS

| | | | |
|---|---|---|---|
| 4,821,594 A | * 4/1989 | Rosheim et al. ......... | 74/490.05 |
| 5,692,412 A | * 12/1997 | Rosheim .................. | 74/490.05 |
| 5,845,540 A | 12/1998 | Rosheim .................. | 74/490.05 |
| 5,967,580 A | 10/1999 | Rosheim ...................... | 294/88 |
| 5,979,264 A | 11/1999 | Rosheim .................. | 74/490.06 |
| 6,105,455 A | 8/2000 | Rosheim .................. | 74/490.06 |
| 6,418,811 B1 | 7/2002 | Rosheim .................. | 74/490.06 |

* cited by examiner

Primary Examiner—David Fenstermacher
(74) Attorney, Agent, or Firm—Kinney & Lange, P.A.

(57) ABSTRACT

A controlled relative motion system having first and second support structures with a controlled output position joint connecting them, and with similar joints on these support structures. One joint is coupled to another controlled relative motion system having an output carrier rotatable in two perpendicular directions through the use of gears therein. This output carrier supports two articulated manipulating systems of which one has a single axis rotatable subbase supporting a rotatable gripping extension, and the other has a shackle connected to a base effector which shackle is supported on a fixed pedestal and another shackle connected to a base effector which shackle is supported on a moveable pedestal.

22 Claims, 15 Drawing Sheets

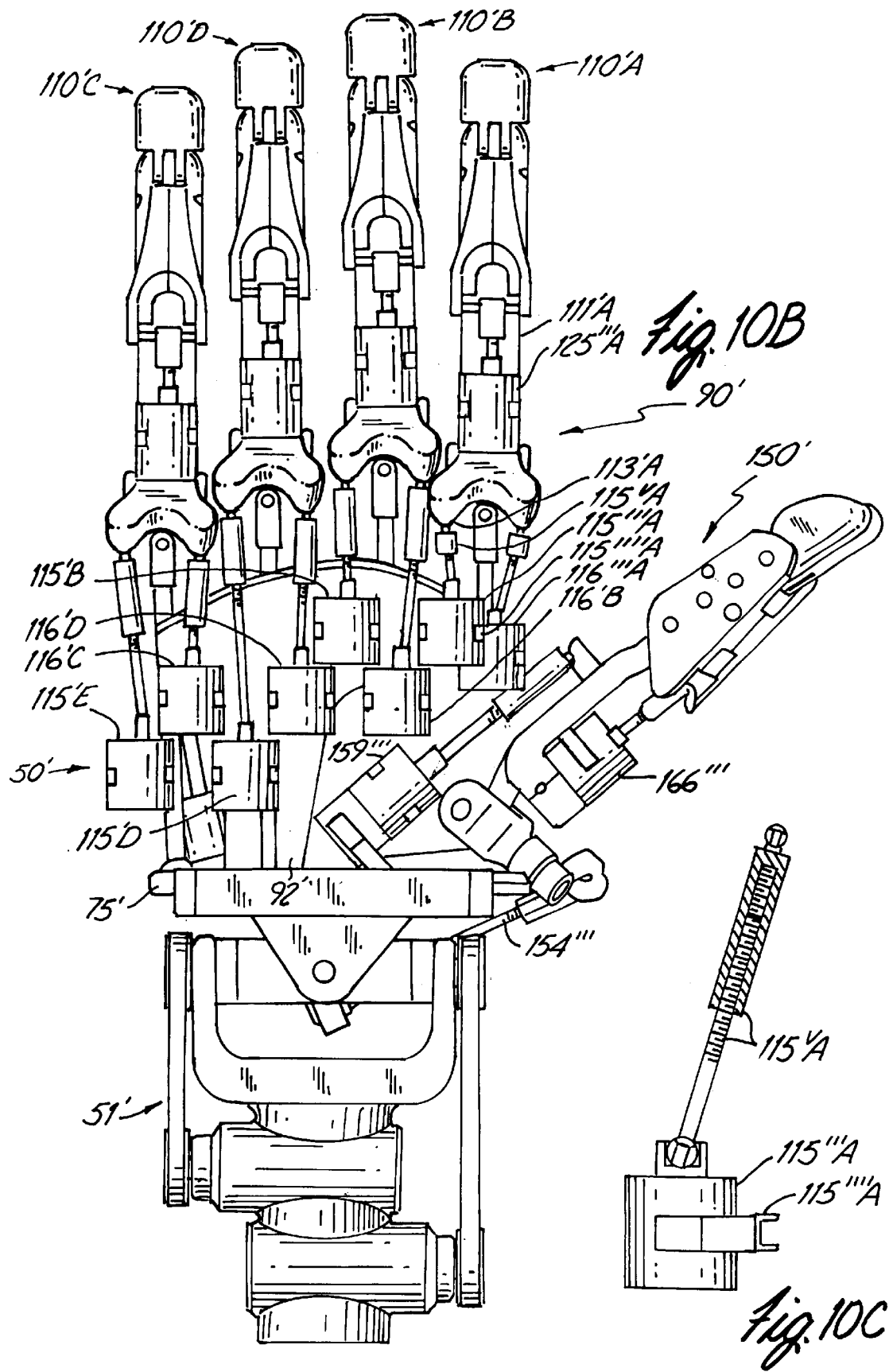

ROBOTIC MANIPULATOR

CROSS-REFERENCE TO RELATED APPLICATION(S)

This application claims the benefit of Provisional Application No. 60/336,477 filed Oct. 31, 2001 for "Robotic Manipulator".

BACKGROUND OF THE INVENTION

The present invention relates to controlled motion mechanical members used as a mechanical manipulator and, more particularly, to a motion controllable, anthropomorphic mechanical manipulator providing some of the capabilities of an upper human torso.

A need for increased automation in the workplace, especially in those workplace environments unsuitable for humans, and a desire to increase the use of animated figures depicting humans or other characters of ten in entertainment situations, has led to substantial efforts in the development of robotics. As a result, substantial advances have occurred in many aspects of robotics.

An important aspect in robotics is the controlling of mechanical manipulators, the portion of a robot used to change the position or orientation of selected objects. In may instances, such manipulators are desired to have motion capabilities similar to those of a human chest, shoulder, arm, wrist and hand, or portions thereof.

Providing a mechanical manipulator simulating such portions of the human torso presents a difficult design problem. The chest portions of a human supporting a shoulder can be considered to have two degrees-of-freedom in motion possibilities available to it, and the shoulder supporting the arm can be considered to have three degrees-of-freedom in motion possibilities available to it. In addition, the elbow can be considered to have a single degree-of-freedom in its possible motion and the wrist can be considered to have three degrees-of-freedom in motion possibilities available for it. Finally, the human palm can be considered to have a degree-of-freedom in its relative motion possibilities while the fingers and thumb thereon can be considered to have four degrees-of-freedom in the motion possibilities thereof.

A number of mechanical joints or mechanical manipulators have been proposed which attempt to exhibit the motion possibilities of the corresponding human joints, and some of these proposals have actually achieved corresponding capabilities to a significant degree. These joints typically have a base on which one side of the joint is fastened, and from which a force imparting arrangement is provided to operate movable members in this fastened portion of the joint. Mechanical transmission arrangements then couple this motion on this fastened side of the joint to the controlled side of the joint to cause that portion to correspondingly move.

However, such joints have of ten been constructed using a substantial number of parts causing significant expense, and with the result that they are of ten difficult to assemble. Further, such joints of ten fail to have the controlled portion thereof exhibit the desired dexterity and range of motion. In addition, the construction have of ten exhibited bulky geometries which do not appear much like those of the human counterparts. Also, control of the controlled side of the joint has of ten been insufficient in the operator not having convenient controlling arrangements available. FIG. 1 shows a joint, mechanical manipulator, or controlled member motion system, 10, which can have a very large output operating range in various configurations over which it is free of singularities, and which is operated by various force imparting devices directly or through various drive trains. A compact, ruggedized version of manipulator 10 is shown in FIG. 1 using yoke and shackle arrangements to rotatably secure the pivoting links provided therein.

Thus, FIG. 1 shows a perspective view of manipulator 10 in which manipulator 10 is positioned on a mounting arrangement, 11, which can be connected with an electric motor arrangement, unseen in these figures, that can rotate mounting arrangement 11 in either the clockwise or counterclockwise direction as selected by the user to thereby carry the remainder of joint or manipulator 10 correspondingly with it in these directions. Directly supported on mounting arrangement 11 is a base support, 12, shown as a rounded corner rectangular solid structure, though different geometrical shapes can be used, having four arms extending out from the main body of the support at the four thickness surfaces thereof initially parallel to the large surfaces of that support, and then bending at right angles away from mounting arrangement 11. These extending arms each thereby form something of a "U" shape to provide a capture space between the main support body of base support 12 and itself to result effectively in a yoke to rotatably accommodate the ends of pivoting links (described below) therein which are secured there by the use of a pin extending through the arm and pivot link end into the main body that allows the pivot link to rotate thereabout. A corresponding shroud plate extends from the main body of support 12 to each of these arms on the side of its capture space opposite the side thereof through which pivoting link secured therein extends to add support to that arm.

Support 12 has an opening, 13, (unseen in FIG. 1) extending along the central axis of rectangular symmetry for support 12 extending out from mounting arrangement 11 to parallel the outer sides of support 12. Opening 13 extends through support 12 and from there through mounting arrangement 11 along the axis about which it is capable of rotating manipulator 10 so as to be capable of permitting some desired means extend therethrough such as electrical wiring, optical fibers or some mechanical arrangement, or some combination thereof.

Also shown supported directly on mounting arrangement 11 are a pair of linear actuator support pedestals, 14, (unseen in FIG. 1) connected to mounting arrangement 11 each of which is shown supporting a linear actuator along with the direct mechanical interconnection between that linear actuator and the remaining portions of manipulator 10. That is, a pair of linear actuators, 15 and 16, are each rotatably mounted in the corresponding one of pedestals 14 by an outer body thereof, 17. Linear actuator 16 has an actuator output shaft, 18, extending from outer body 17 thereof which is directly affixed to a clevis, 19. Clevis 19 on output shaft 18 of linear actuator 16 is directly and rotatably affixed to a pivoting link, 20, by a further pin, 21, through an opening in a boss, 22, extending from pivoting link 20 (which pin may be in bearings or a bushing mounted in boss 22 positioned about the opening therein). Linear motion by output shaft 18 in actuator 16 outward or inward causes clevis 19 to correspondingly move away from or toward body 17 of linear actuator 16.

Such motions by clevis 19 forces pivoting link 20 to in turn rotate one way or the other about a pin, 23, around a rotation axis extending through pin 23 that is more or less perpendicular to the length of link 20. Pin 23 is directly affixed in an opening in the central rectangular portion of base support 12 and in an opening in an extending arm of base support 12 as two sides of a yoke to extend through the capture space therebetween and through an opening in the end of pivoting link 20 (which pin may be in bearings or a bushing mounted in the opening in link 20, and pin 23 could be a pivot screw (shoulder bolt) rather than a pin. Such a pivot screw is threaded at the end thereof opposite the screw head only a relatively short distance in from that end to permit its being screwed firmly into base support 12 but only a fixed distance therein to assure a selected length of the screw is exposed outside support 12 The surface of this exposed portion of the screw from support 12 to the screw head is smooth especially if no bearing or bushing is used between this screw and pivoting link 20 lubrication at the least would be likely to be used in this situation).

An identical linear actuator translation drive system for forcing rotational motion of another pivoting link is provided in connection with linear actuator 15. As seen in FIG. 1, a clevis, 19', is affixed to output shaft 18 of linear actuator 15 with the other end of clevis 19' being affixed by a pin, 21', to a further pivoting link, 20', rotatably connected to base support 12, through an opening in a boss, 22', extending from pivoting link 20'. Thus, again, linear motion by output shaft 18 in actuator 15 outward or inward causes clevis 19' to correspondingly move away from or toward body 17 of linear actuator 15 which forces pivoting link 20' to correspondingly rotate in either a clockwise or counterclockwise direction. Pivoting link 20' can rotate on bearings about a pin or screw, 23', not seen in these figures, positioned in an opening therein at its end with pin or screw 23' affixed to the sides of the corresponding yoke in base support 12, and pivoting link 20' again rotates around an axis extending therethrough more or less perpendicular to the length of link 20'.

Pivoting links 20 and 20' are two pivoting links in a plurality of lower pivoting links in manipulator 10, this lower plurality further including two other pivoting links, 20" and 20''' (not all seen in FIG. 1), with extending bosses, 22" and 22''' (not all seen in FIG. 1). Bosses 22" and 22''' are unused in the present situation in which just two linear actuators are used to operate manipulator 10, but can be used with the use of further linear actuators. These last two pivoting links are each capable of rotating on bearings about a corresponding one of pins or pivot screws, 23" and 23''' (not all seen in FIG. 1), respectively, with the corresponding axis of rotation extending therethrough substantially perpendicular to the length of links 20" and 20'''. Pins or pivot screws 23" and 23''' are again directly affixed in a corresponding opening in the central rectangular portion of base support 12 and in a corresponding opening in a corresponding extending arm of base support 12 in the capture space therebetween (which pin may be in bearings or a bushing mounted in each of these base support 12 openings so as to be positioned about that opening, and pin 23 could be a pivot screw rather than a pin). Each of pins or pivot screws 23, 23', 23" and 23''' is affixed to base support 12 such that the corresponding one of the plurality of lower pivoting links rotatably coupled to base support 12 thereby rotates about an axis therethrough that intersects, and is perpendicular to the axis of rectangular symmetry of support 12 extending out from mounting arrangement 11, with these rotation axes being separated from adjacent ones by equal angles measured about the symmetry axis, here 90°.

The lower plurality of pivoting links 20, 20', 20" and 20''', in addition to each having an end thereof being rotatably connected to base support 12 by the yokes effectively provided by the central rectangular portion and the corresponding extending arm of that base support as described above, also each have the opposite end thereof formed as devises with two spaced apart arms that are rotatably connected by four further pins or pivot screws, 24, 24', 24" and 24''', to corresponding pivot holder shackle members, 25, 25', 25" and 25'''. Each of these pivoting link devises has a shroud plate extending between the arms thereof on the side opposite that through which a corresponding shackle extends to add support to these two arms. Each of these pivot holder shackle members is formed as a bent link with an opening therethrough at each end to accept a pin extending through it (which pin may be in bearings or a bushing mounted in the link opening positioned about that opening therein), the bend in the link occurring along the width thereof between the two openings each provided near a corresponding end thereof. Each of these pivot holder shackle members 25, 25', 25" and 25''' has an end thereof captured in a shrouded clevis at the end of a corresponding one of the lower plurality of pivoting links 20, 20', 20" and 20''' by a corresponding one of pins 24, 24', 24" and 24''' extending through the opening in that bent link end into the arms of the pivoting link clevis on either side thereof.

The axis of rotation of each of the lower plurality of pivoting links 20, 20', 20" and 20''' through a corresponding one of pins or pivot screws 24, 24', 24" and 24''' in being rotatably coupled to a corresponding one of pivot holder shackle members 25, 25', 25" and 25''', and the axis of rotation of each of these links through a corresponding one of pins or pivot screws 23, 23', 23" and 23''' in being rotatably coupled to base support 12 are, in each link instance, perpendicular to planes therethrough that for each link intersect one another at substantially right angles. These rotation axes for each of these pivoting links are also oriented in directions differing from those in an adjacent pivoting link, i.e. the next pivoting link thereafter around base support 12. This allows pivot holder shackle members 25, 25', 25" and 25''' to be moved by the corresponding pivoting links substantially with respect to base support 12, but for the same length links these pivot holder shackle members will always be in a plane common thereto, and will move about a circle in such planes. Although pivot holder shackle members 25, 25', 25" and 25''' are shown in these figures as extended bent links, this shape is not required but instead other geometrical shapes could be used.

Manipulator 10 is shown in these figures having a further upper plurality of pivoting links. Each of this plurality has an end thereof formed as a clevis formed by two spaced apart arms that is rotatably coupled to each of pivot holder shackle members 25, 25', 25" and 25''' by a corresponding one of a further set of pins or pivot screws, 27, 27', 27" and 27''' (not all seen in FIG. 1) extending through the other end opening of such pivot holder shackle member not connected to a lower pivoting link to be affixed to the two arms of the clevis (which pin may be in bearings or a bushing mounted in the link opening positioned about that opening therein). Again, each of these pivoting link devises has a shroud plate extending between the arms thereof on the side opposite that through which a corresponding shackle extends to add support to these two arms by forming a shrouded clevis.

The axis of rotation of the corresponding one of this upper plurality of pivoting links, in being able to rotate about its pin or pivot screws 27, 27', 27" and 27''', is directed so as to be more or less parallel to the length of the link. There is a corresponding one of a set of angles, 28, 28', 28" and 28''', (not all seen in FIG. 1) of a selected angular magnitude between the axis of rotation of the pivoting link from the lower plurality thereof rotatably connected to each pivot holder member and the axis of rotation of the one of the upper plurality of pivoting links also rotatably connected thereto as shown in these figures set by the bend in the bent links forming the pivot holder shackle members. The selection of the magnitude of each of angles 28, 28', 28" and 28'" effects the capabilities of manipulator 10 as will be described below.

Another set of pins or pivot screws, 29, 29', 29" and 29'", (not all seen in FIG. 1) are each used at the opposite end of a corresponding one of such an upper plurality of pivoting links, 30, 30', 30" and 30'" (not all seen in FIG. 1). If manipulator 10 is constructed symmetrically above and below a plane including each of pivot holder shackle members 25, 25', 25" and 25'", i.e., angles 28, 28', 28" and 28'" in these figures being bisected by such a common plane, the upper plurality of pivoting links 30, 30', 30" and 30'" can be identical in construction with each other and with each of the lower plurality of pivoting links 20, 20', 20" and 20'". Although this is a significant economic factor in manufacturing significant numbers of joint or manipulator 10, this symmetry is not required for successful operation of such manipulators. However, the nature of the positioning of the output structure in such manipulators for a given rotation of the rotor shafts of motors 15 or 16 will change with differences in the portions of angles 28, 28', 28" and 28'" above and below the horizon. Also, the lengths of pivoting links in the upper and lower pluralities thereof need not all be the same to have successful operation of manipulator 10 but, again, the pattern of the positioning of this output structure will change depending on such differences.

The output structure which is controlled in manipulator 10 by motion of linear actuators 15 and 16 has a hole, 31, provided therethrough to form a rounded corner rectangular solid, open center structure, though different geometrical shapes can be used, resulting in a manipulable support, 32. Manipulable support 32 has four arms extending out from the main body of the support at the four thickness surfaces thereof initially parallel to the large surfaces of that support, which then bend away at right angles generally toward mounting arrangement 11. These extending arms each thereby form something of a "U" shape to provide a capture space between the main support body of manipulable support 32 and itself to result effectively in a yoke to rotatably accommodate the ends of the upper pivoting links therein which are secured there by the use of the corresponding one of pins 29, 29', 29" and 29'" extending through the arm and pivot link end into the main body that allows the pivot link to rotate thereabout. A corresponding shroud plate extends from the main body of support 32 to each of these arms on the side of the arm capture space opposite the side thereof through which the corresponding pivoting link secured therein extends to add support to that arm.

Again, various items can be extended through opening 31 such as electrical wiring or optical fibers or, in this output situation, a further mechanical device supported on support 32, or some combination of such features or other alternatives. Also, the output structure as represented by manipulable support 32 can be controlled in manipulator 10 by motion of a complementary set of linear actuators, 35 and 37, (not seen in FIG. 1 but referenced here to clarify certain subsequent figures) having their bases mounted in actuator support pedestals 14 and their output shafts connected to the two remaining lower pivoting links 20" and 20'" either instead of using actuators 16 and 15 connected to lower pivoting links 20 and 20' as described above, or alternatively also using actuators 15 and 16 to provide greater force and stability.

Each of pivoting links 30, 30', 30" and 30'" in the upper plurality thereof is rotatably coupled by a corresponding one of pins or pivot screws 29, 29', 29" and 29'" to manipulable support 32. Here too, each of the plurality of upper pivoting links can rotate on bearings about a corresponding one of pins or pivot screws 29, 29', 29" and 29'" positioned in an opening therein at its end with the corresponding one of pins 29, 29', 29" and 29'" affixed to the sides of the corresponding yoke in manipulable support 32, and each of pivoting links 30, 30', 30" and 30'" again rotates around an axis extending therethrough more or less perpendicular to the length thereof. These rotation axes are separated from adjacent ones by equal angles measured about the symmetry axis, here again 90° because of the presence of four pivot links. Although the rotation axes of the pivoting links at the rotary couplings thereof to supports 12 and 32 are described as making equal angles with adjacent ones thereof as they occur about those supports, these angles need not be identical about either support, nor identical about one support with those about the other, to be able to position support 32 over a substantial angular range, though providing substantially such identities is of ten convenient.

Pivoting links 30, 30', 30" and 30'" in the upper plurality thereof may be connected to the side of manipulable support 32 that is opposite to the side of base support 12 to which the corresponding one of pivoting links 20, 20', 20" and 20'" in the lower plurality thereof is connected as shown in FIG. 1 or, alternatively, connected to manipulable support 32 on the same side thereof as the side of base support 12 to which the corresponding one of pivoting links 20, 20', 20" and 20'" in the lower plurality thereof is connected. The axis of rotation of such a one of pivoting links 30, 30', 30" and 30'" in the upper plurality thereof about its pin or pivot screw coupling it to support 32 extends through that pin or screw more or less perpendicular to the direction of the length of that link, and substantially parallel to the axis of rotation about the pin or pivot screw rotatably coupling the corresponding one of pivoting links 20, 20', 20" and 20'" in the lower plurality thereof to base support 12. The correspondence here between upper and lower plurality pivoting links is established by each being coupled to the same one of pivot holder members 25, 25', 25" and 25'". Again here, as for the pivoting links in the lower plurality thereof, the axis of rotation of one of pivoting links 30, 30', 30" or 30'" in the upper plurality thereof about its corresponding one of pins or pivot screws 27, 27', 27" or 27'" is substantially perpendicular to a plane which intersects at substantially right angles that further plane which is substantially perpendicular to the axis of rotation of that link about its corresponding one of pins 29, 29', 29" or 29'".

The various structural components of joint or manipulator 10 described in connection with FIG. 1 above are typically formed of a metal or metals, or alloys thereof, appropriate for the intended use, i.e. perhaps stainless steel for a medical use, aluminum or titanium where weight is a primary concern, etc. Many or all of these components could be molded polymeric materials instead.

The center of manipulable support 32 can essentially reach every point on a hemispherical surface about manipulator 10 (and in many link constructions, somewhat beyond such a surface) without the occurrence of loss of control singularity points anywhere in this range of motion. During such motion, as indicated above, pivot holder shackle members 25, 25', 25" and 25'" will always intersect a common plane though a different plane at each location of manipulable support 32. Thus, there is a desire to use manipulator 10 with these capabilities, and to use other robotic structure improvements, to simulate portions of the human body.

BRIEF SUMMARY OF THE INVENTION

The present invention provides a controlled relative motion system having first and second support structures, the first support structure having a first support offset structure extending along a first axis and the second support structure having a second support offset structure extending along a second axis, connected with an intermediate joint having a base member and a controlled position member that has an output carrier which can be angularly positioned with respect to the base member anywhere over a selected spatial surface. This intermediate joint base is affixed to an interior end of a selected one of the first and second support offset structures with the output carrier affixed to an interior end of that one remaining. A similar first support joint has a base member supported by and affixed with respect to the first support offset structure at an exterior end thereof opposite its interior end along the first axis. A second support joint, also similar to the intermediate joint, has a base member supported by and affixed with respect to the second support offset structure at an exterior end thereof opposite the interior end thereof along the second axis.

One of the first and second support joints as a base is coupled to a further controlled relative motion system having an extended open interior member rotatably coupled to the base for rotating about a corresponding interior member rotation axis along which a pair of spaced apart interior member sides extend so as to have an extended space therebetween. The extended open interior member is rotatably coupled to the base at an end thereof joining the interior member sides at one end of the extended space by a first shaft coupled thereto, and is further rotatably coupled to the base at an opposite end thereof also joining the interior member sides at an opposite end of the extended space by a second shaft coupled thereto.

Also, an output carrier has a pair of output carrier sides spaced apart by a recess space with these output carrier sides being joined in a joining structure on one side of the recess space. The output carrier is positioned to have the extended open interior member in its recess space so that the output carrier sides extend at least in part substantially parallel to the interior member sides to which they are rotatably coupled to rotate about a corresponding output carrier rotation axis substantially perpendicular to the interior member rotation axis. The output carrier is rotatably coupled to the extended open interior member by a follower shaft affixed to the output carrier and rotatably coupled to the extended open interior member.

An interior member first bevel gear is located in the extended space and affixed to the first shaft, and an output carrier first bevel gear is located in the extended space and affixed to the follower shaft to be engaged with the interior member first bevel gear. A plurality of force imparting means is mounted in the base with each of the first and second shafts being rotatably coupled to a corresponding one of these force imparting means.

This further controlled motion system with the output carrier as a base supports an articulated manipulating system capable of engaging selected objects having a subbase rotatably mounted on the base to have a single subbase rotation axis therethrough. A first linear actuator is coupled at one end thereof to the base and coupled at an opposite end thereof to the subbase to be capable of rotating the subbase about the subbase rotation axis. A first effector base is rotatably connected to the subbase to have a first effector rotation axis, and a second linear actuator is coupled at one end thereof to the subbase and coupled at an opposite end thereof to the first effector base to be capable of rotating the first effector base about the first effector rotation axis.

This further controlled motion system with the output carrier as a base also supports a shackle having a pair of arms spaced apart by a recess space which arms are joined in a joining bar on one side of the recess space, an effector base rotatably mounted at a pivot location thereof to and between the separated arms of the shackle so as to leave a recess space between an end of that effector base rotatably mounted to the shackle and the joining bar thereof, a pedestal affixed to the base relatively near to where the subbase is rotatably mounted on the base and having the joining bar of the shackle rotatably coupled thereto. A gripping extension is rotatably coupled to the effector base at an extension coupling location thereof spaced apart from the pivot location thereof, and an extension linear actuator is positioned adjacent to the effector base and coupled at one end thereof so as to have that end positioned at least in part in the recess space of the shackle with that remaining end of the linear actuator rotatably coupled to that gripping extension. Further, a pair of effector linear actuators is provided with each having an end thereof connected to the base at corresponding base connection locations thereon, and each having that opposite end thereof rotatably connected to an effector base at corresponding effector connection locations thereon. Thus, any substantial differentials in movement of these actuators cause corresponding substantial motions of the effector base towards a corresponding one of the base connection locations and so that substantial common movements of these actuators causes substantial motions of the effector base toward or away from both of the base connection locations.

DETAILED DESCRIPTION

Figure 1:
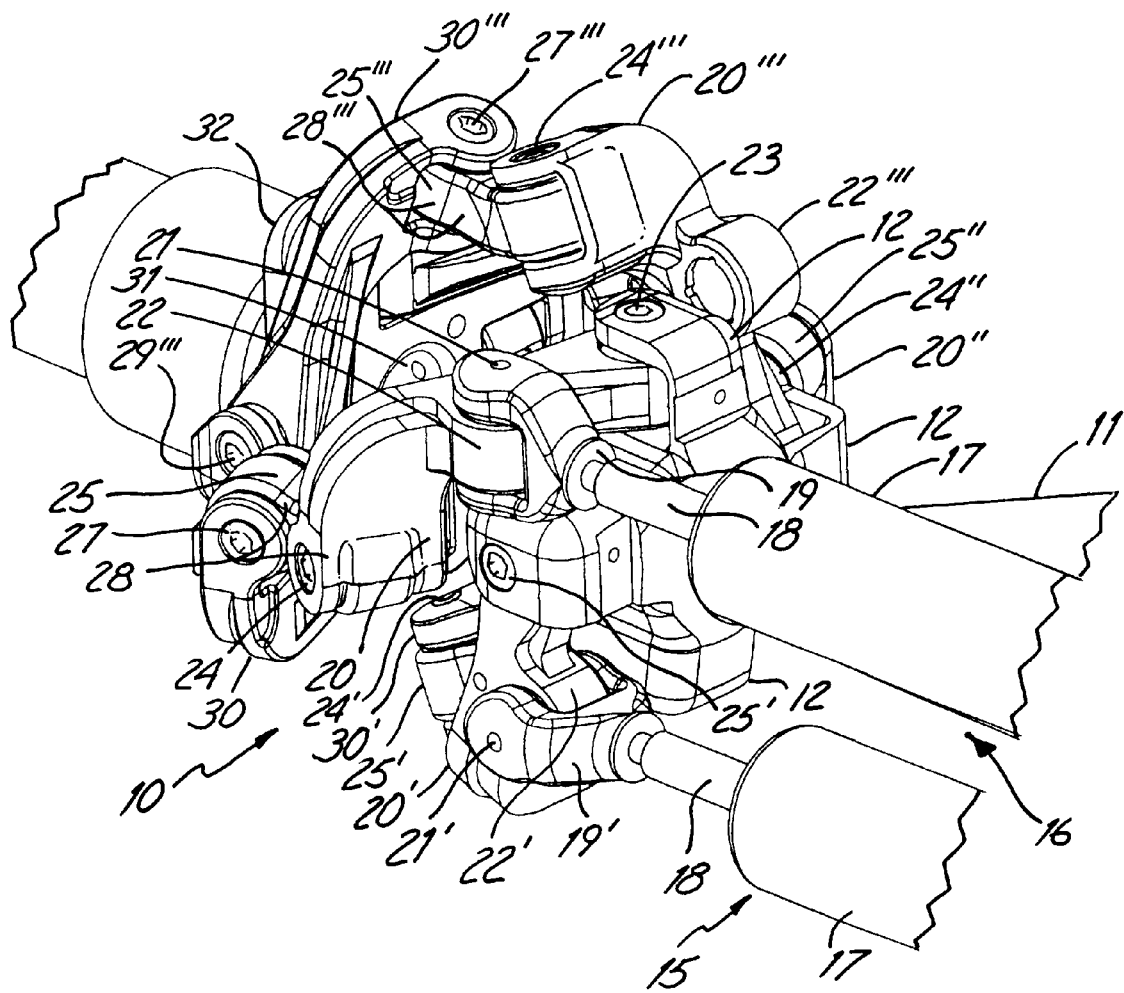
FIG. 1 shows a perspective view of a robotic manipulator used in the present invention.
Figure 2:
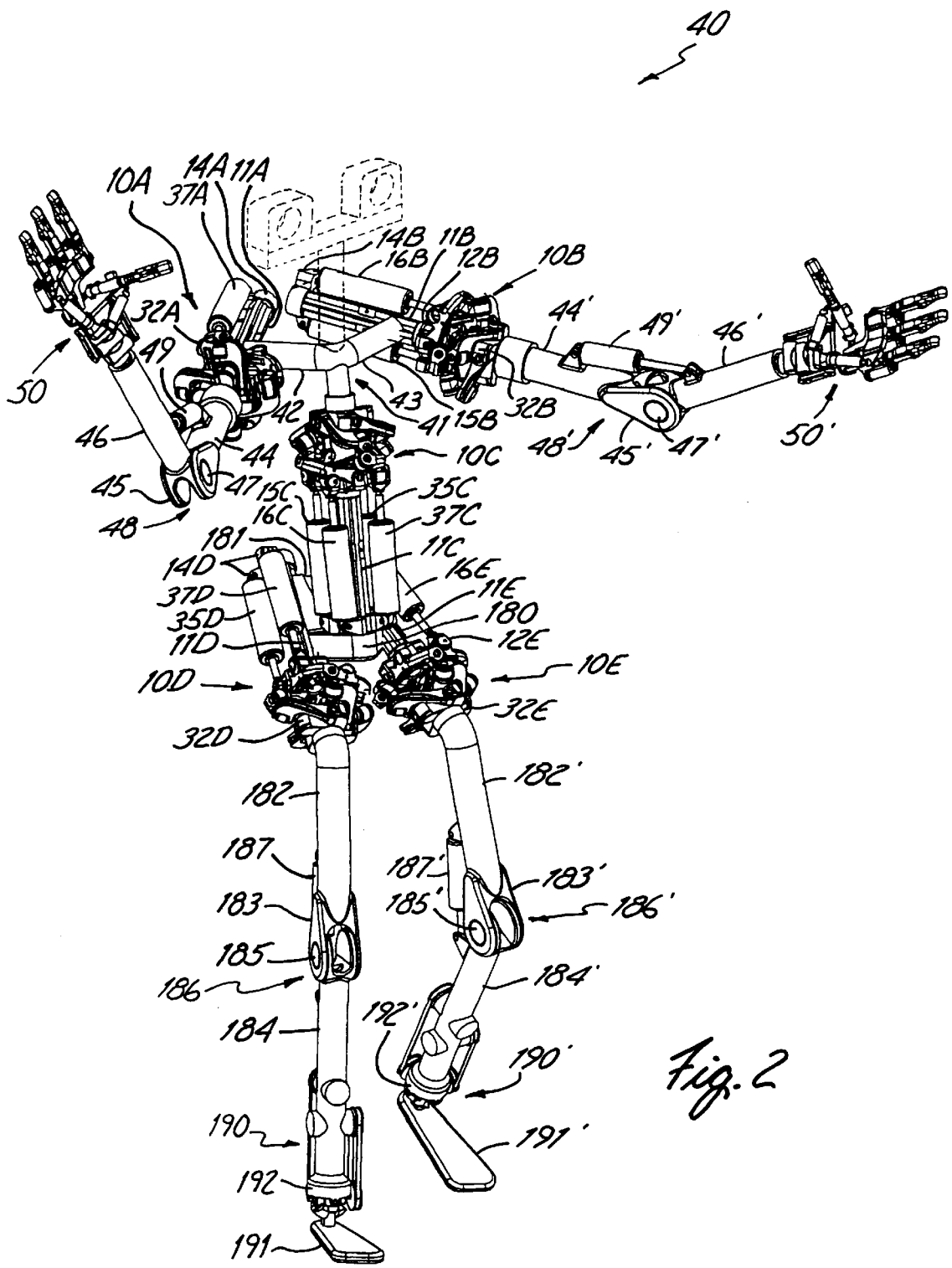
FIG. 2 shows a perspective view of a robot of the present invention simulating a human body.

Manipulator, or joint, 10 of FIG. 1 is a very effective controlled output manipulator for use in simulating the motion possibilities of the two degree of freedom joints and other bending structures of the human body. FIG. 2 shows a robot, 40, reminiscent of the human body with such joints used therein to simulate human shoulders, middle upper torso and hips, and another such manipulator could be added to simulate the neck though not shown.

A control arrangement for robot 40 is operated under the direction of a computer which typically controls operation of a system controller, not shown. This controller has a transmitter therein to transmit information signals to a receiver in robot 40, again not separately shown, but which might be located in a portion of that robot in the position of a human head indicated to some extent by a dashed line rendering. This portion of robot 40 also has a transmitter therein for transmitting information signals to the controller which has a further receiver to receive same therein. Alternatively, or as a supplemental control arrangement, other transmitters or receivers, or both, which can interact with the transmitter or receiver, or both, in robot 40 can be provided in items such as household appliances to facilitate robot 40 interacting with them to reduce the control and sensing apparatus that otherwise needs to be provided in robot 40 to support such interaction. Thus, for instance, a robot used to fetch items from a refrigerator might not need a simulated vision system to accomplish such tasks if the refrigerator itself can provide sufficient guide signals to the robot, or at least not as advanced a system as would be required in the absence of such refrigerator based robot guidance. Wiring arrangements are provided through the joints and joint connectors in robot 40 to distribute signals obtained from the receivers therein to the actuators therein intended to respond to them, and to collect signals from sensors therein to be brought to the transmitters therein.

Figure 3:
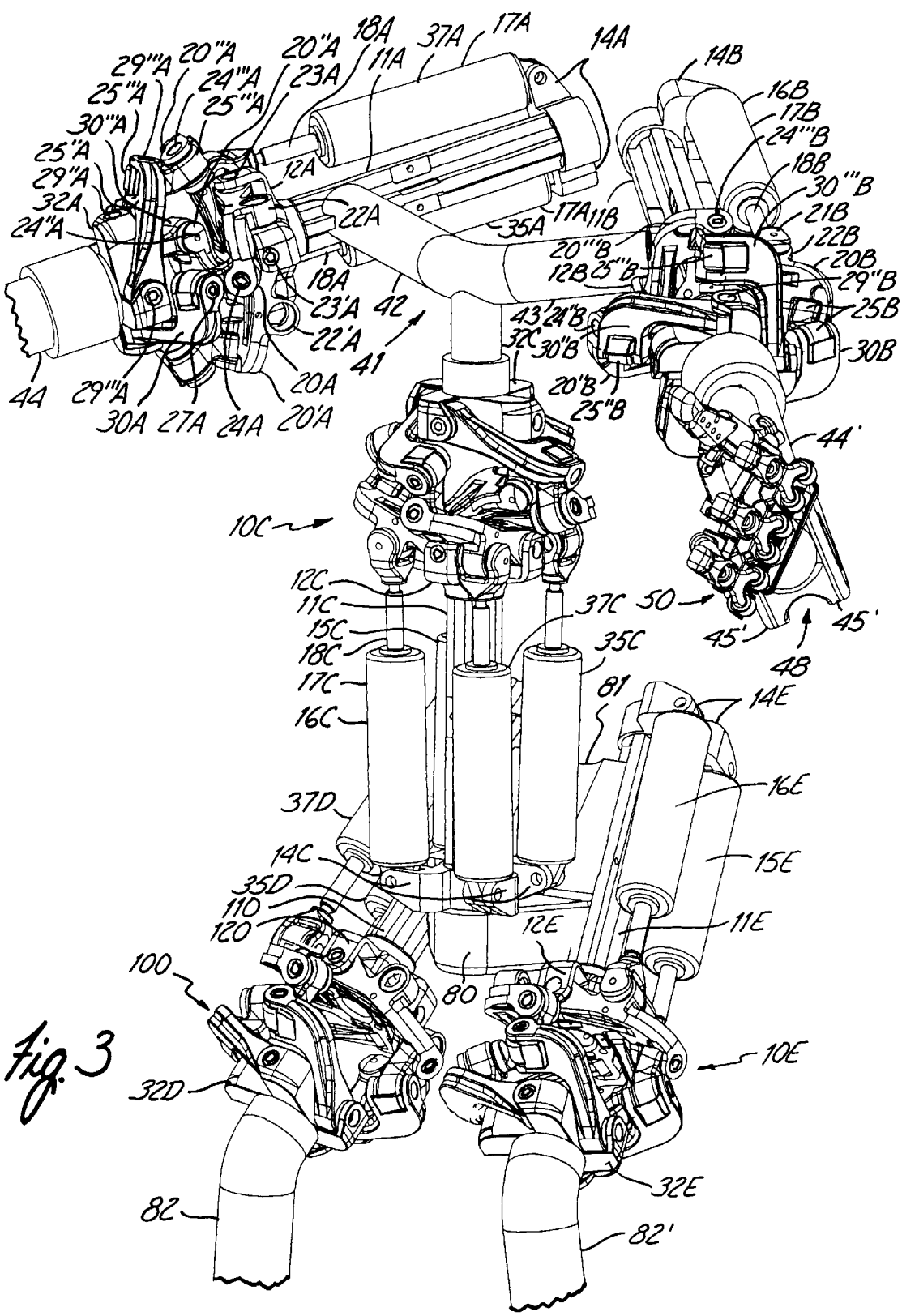
FIGS. 3, 4, 5 and 6 show perspective views of portions of the structure shown in FIG. 2.

A "tee" structure, 41, in the upper portion of robot 40 in FIG. 2, as shown in more detail in FIG. 3, has the two arms, 42 and 43, of the crosspiece each canted rearward from the base joining point to be out of alignment with one another so as to form an angle therebetween of less than 180°. Arm 42 has a manipulator, 10A, like manipulator 10 of FIG. 1, useful for simulating a human right shoulder, mounted to the end thereof at a right angle to the long axis of mounting arrangement 11A of manipulator 10A near its connection to base support 12A (unseen in FIG. 2). Linear actuators 35A and 37A (connected to lower pivoting links 20" A and 20'" A rather than to lower pivoting links 20A and 20' A in the manner of linear actuators 16 and 15 in FIG. 1 being connected to lower pivoting links 20 and 20' there) are mounted on support pedestals 14A on mounting arrangement 11A and connected to the corresponding lower pivoting links which can cause manipulable support 32A of manipulator 10A to move to simulate selected right human shoulder motion under direction of the controller.

Manipulable support 32A is connected to an upper arm bar, 44, which has at its opposite end a yoke, 45, in which a forearm bar, 46, is rotatably connected by a pair of pin-like bosses, 47, each extending through a yoke arm opening to be affixed in the sides of the upper arm bar yoke thereby forming a single degree of freedom joint, 48, simulating a human elbow. A linear actuator, 49, is connected between upper arm bar 44 and forearm bar 46 to operate that joint by causing forearm bar 46 to selectively rotate in yoke 45 about pin-like bosses 47. A motor and a rotational joint arrangement contained within upper arm bar 44 allows it to be rotated over an angular range with respect to manipulator 10A. A joint and manipulator structure, 50, simulating a human wrist and hand is mounted on the end of forearm bar 46, and a motor and a rotational joint arrangement contained within forearm bar 46 allows joint and manipulator structure 50 to be rotated over an angular range with respect to forearm bar 46.

Figure 4:
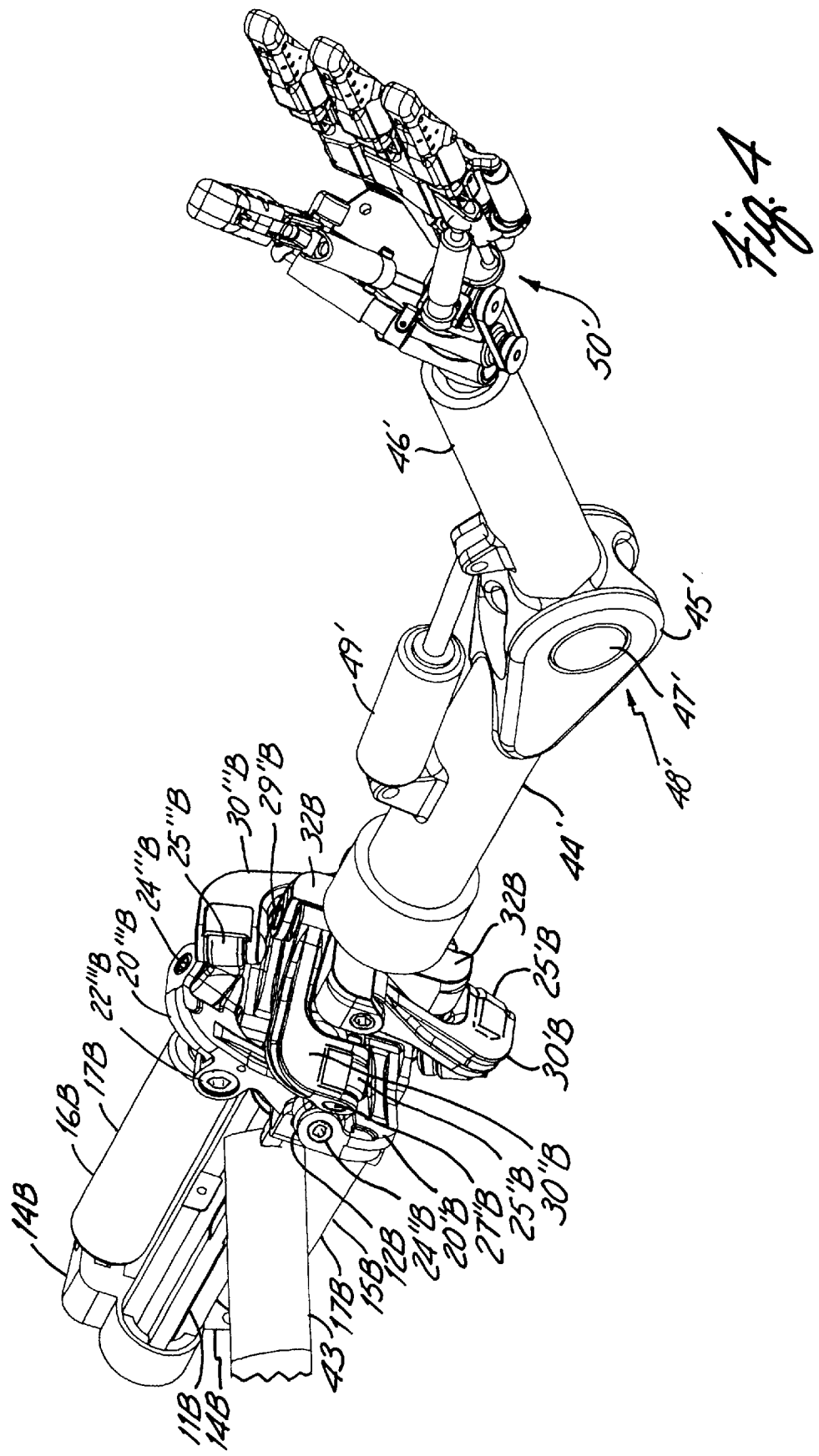

Similarly, as shown in FIG. 2 and in more detail in FIGS. 3 and 4, arm 43 has a manipulator, 10B, like manipulator 10 of FIG. 1, useful for simulating a human left shoulder, mounted to the end thereof at a right angle to the long axis of mounting arrangement 11B of manipulator 10B near its connection to base support 12B. Linear actuators 15B and 16B are mounted on support pedestals 14B on mounting arrangement 11B and connected to the corresponding lower pivoting links which can cause manipulable support 32B of manipulator 10B to move to simulate selected left human shoulder motion under direction of the controller.

Manipulable support 32B is connected to an upper arm bar, 44', which has at its opposite end a yoke, 45', in which a forearm bar, 46', is rotatably connected by a pair of pin-like bosses, 47', each extending through a yoke arm opening to be affixed in the sides of the upper arm bar yoke thereby forming a single degree of freedom joint, 48', simulating a human elbow. A linear actuator, 49', is connected between upper arm bar 44' and forearm bar 46' to operate that joint by causing forearm bar 46' to selectively rotate in yoke 45' about pin-like bosses 47'. A motor and a rotational joint arrangement contained within upper arm bar 44' allows it to be rotated over an angular range with respect to manipulator 10B. A joint and manipulator structure, 50', simulating a human wrist and hand is mounted on the end of forearm bar 46', and a motor and a rotational joint arrangement contained within forearm bar 46' allows joint and manipulator structure 50' to be rotated over an angular range with respect to forearm bar 46'.

Figure 5:
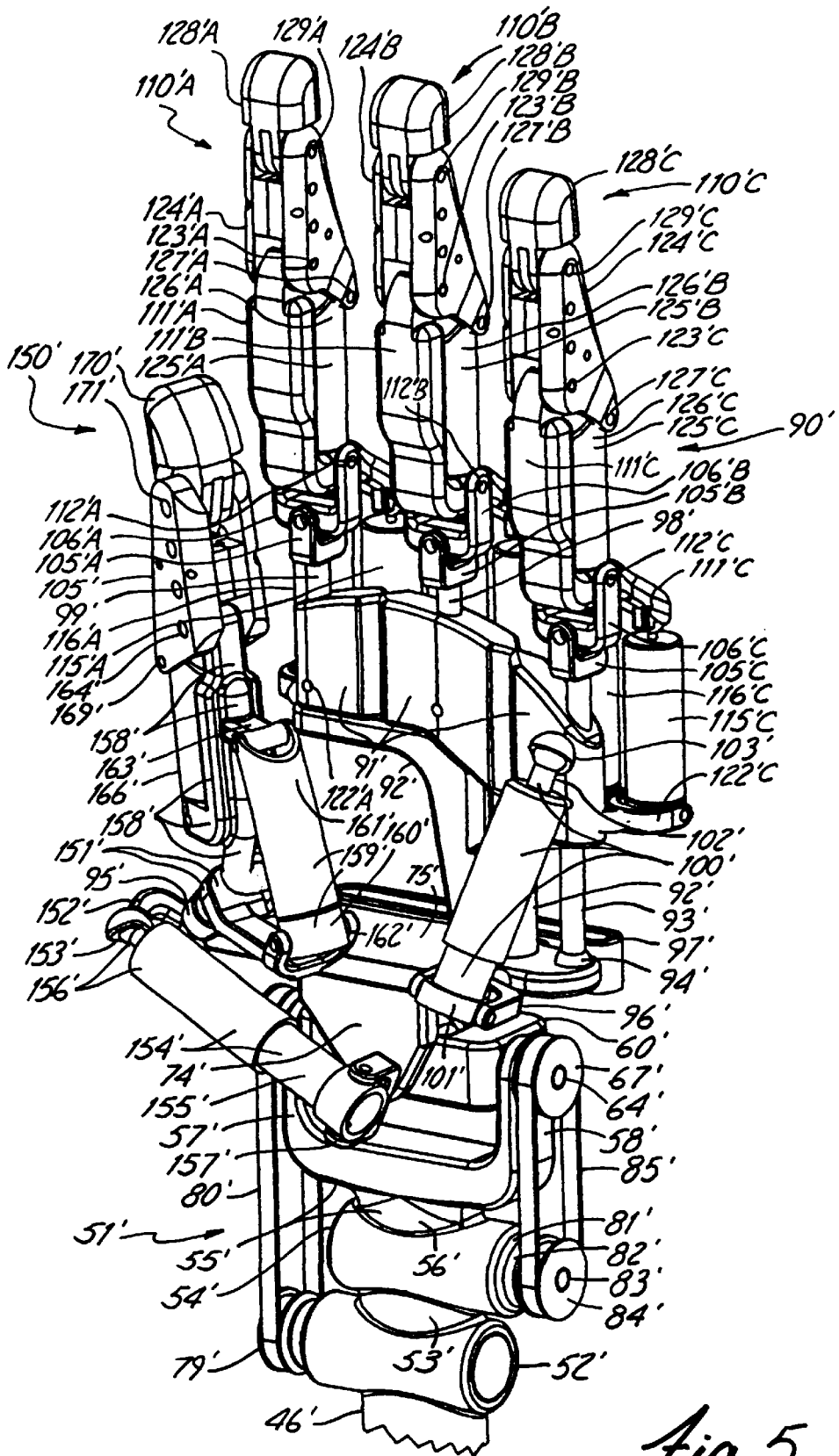

FIG. 5 shows a perspective view of joint and manipulator structure 50' for simulating a human wrist and hand mounted on the end of forearm bar 46'. A two degree of freedom positioning joint, 51', for simulating a human wrist has a truncated cylindrical shell shaped motor housing, 52', affixed to the end of forearm bar 46' with its axis of radial symmetry oriented perpendicular to the long axis of forearm bar 46' (structures in joint and manipulator structure 50 mounted on the end of forearm bar 46 similar to those in joint and manipulator structure 50' mounted on the end of forearm bar 46' have the same numerical designations there as they do in joint and manipulator structure 50' but without the following prime mark). Typically, motor housing 52' has one end open to receive an electrical motor therein with the other end closed. (Positioning joint 51' can be made a three degree of freedom joint by providing a motor on, and a rotatable connection in, forearm bar 46' to thereby permit rotating joint and manipulator structure 50' including positioning joint 51' about the long axis of forearm bar 46').

An intermediate stem portion, 53', is affixed at one end thereof to motor housing 52' to extend therefrom perpendicular to the housing axis of radial symmetry, and also affixed at its other end to another truncated cylindrical shell shaped motor housing, 54', having its axis of radial symmetry oriented parallel to that of motor housing 52'. However, motor housing 54' has the end thereof open to receive an electrical motor therein being adjacent to the closed end of motor housing 52' so as to be on the opposite side of intermediate stem portion 53' from the open end of motor housing 52' that is open for the same purpose, and typically, again, the other end of motor housing 54' is closed.

Forearm bar 46' and intermediate stem portion 53' typically have openings extending therethrough to allow control wiring to be installed. Motor housing 52', in addition to having some of such wiring terminate there for the motor to be provided therein, also has sufficient space therein to allow such wiring to pass from forearm bar 46' to intermediate stem portion 53' to reach motor housing 54' for the motor to be provided there. Additional wiring, or other facilitating means, may also be passed through such openings and spaces if needed.

A clevis, 55', is affixed to motor housing 54' to have its stem portion, 56', extend from that motor housing perpendicular to the housing axis of radial symmetry. Stem portion 56', in so extending, subsequently diverges therealong into two spaced apart arms, 57' and 58', as can be better seen in the rear perspective view of FIG. 6. These diverging arm structures first curve away from each other approximately perpendicularly to stem portion 56' and then further extend to again curve at more or less right angles to thereby parallel one another with a space therebetween (i.e. the arms together follow approximately a "U" shape supported on the clevis stem portion). An opening is provided in the ends of each of these arms across the space between the arms from one another so that they share the same axis of radial symmetry parallel to those of housings 52' and 54'.

Figure 6:
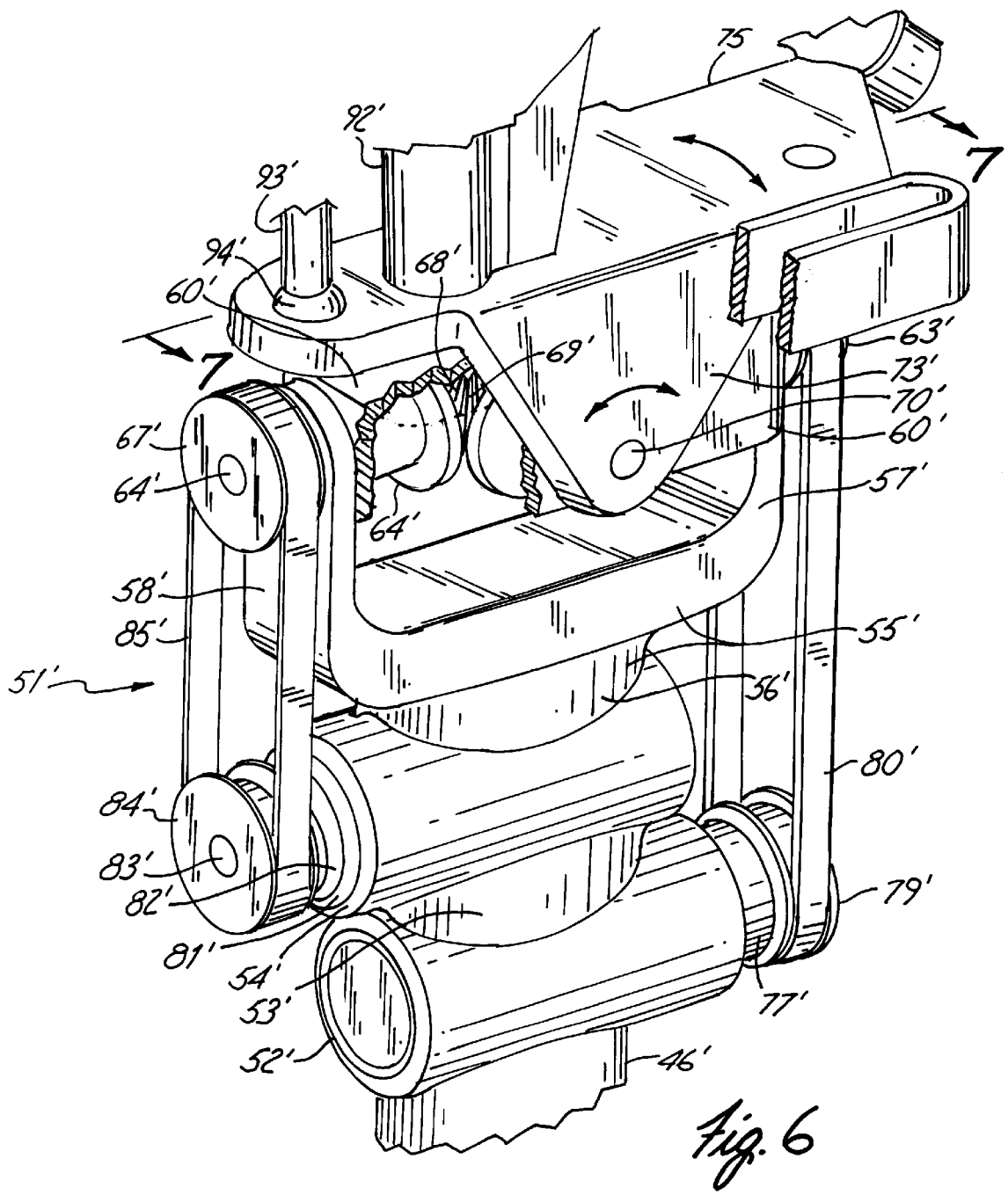

A rotatable bridge carrier, 60', is positioned between clevis arms 57' and 58', and is shaped approximately in the form of a rectangular solid shell with the bottom side thereof in FIGS. 5 and 6 omitted as better seen in FIG. 6 as a result of the cut away provided in carrier 60' there. As best seen in the section view of FIG. 7A, taken at the position indicated in FIG. 6, carrier 60', across from the opening in the end of clevis arm 57' in which there is positioned a bushing, 61', has the end of a cylindrical shaft, 62', affixed thereto at a short side thereof centered along its width. Shaft 62' extends through bushing 61' to be positioned in the opening in clevis arm 57' to thereby have clevis arm 57' rotatably support carrier 60' at one of the two short sides thereof. Shaft 62' also extends beyond clevis arm 57' to have a pulley, 63', affixed to the remaining end thereof.

The remaining short side of carrier 60', across from the short side thereof from which shaft 62' extends, has an opening therein centered along the width thereof that is across from the opening in the end of clevis arm 58' to have a common axis of radial symmetry. A further cylindrical shaft, 64', extends through a bushing, 65', positioned in the opening of the remaining short side of carrier 60', and through a bushing, 66', of clevis arm 58' to extend past clevis arm 58' to have a further pulley, 67', affixed to the end thereof. The portion of shaft 64' extending into the interior opening in carrier 60' extends to a bevel gear, 68', and has a diameter increase between just inside the short wall of carrier 60' and bevel gear 68' resulting in a larger cylindrical shaft portion in the interior of carrier 60' to thereby serve to retain that shaft within the interior of carrier 60'. Clevis arm 58' thus rotatably supports carrier 60' at the remaining one of the two short sides thereof so that clevis 55' and carrier 60' together form a revolute joint having an axis of rotation that includes the parallel, end-to-end axes of radial symmetry of shafts 62' and 64'.

Bevel gear 68' in the interior opening of carrier 60' meshes with a further bevel gear, 69', positioned around a further cylindrical shaft, 70'. Each of the two long sides of carrier 60' across from one another has an opening therein opposite the other centered along the lengths of those sides such that the common axis of radial symmetry of these two openings intersects, and is perpendicular to, the common axis of radial symmetry of the two openings in the short sides of carrier 60'. These long side openings each has therein a corresponding one of a pair of bushings 71' and 72', through and past which shaft 70' extends to have its ends each affixed to the adjacent wall provided by a corresponding one of spaced apart flange sides, 73' and 74', of an output positioner, 75', so that carrier 60' across its width is positioned between flange sides 73' and 74'. Output positioner 75' is thus rotatably supported by carrier 60' so they together form a further revolute joint having an axis of rotation that is common with the axis of radial symmetry of shaft 70'. Flange sides 73' and 74' of output positioner 75' extend parallel to one another with the space therebetween being maintained in addition to shaft 70' by an output support plate affixed to the ends of the flange sides opposite those ends thereof near to the corresponding connections of the ends of shaft 70'.

This open chain of two revolute joints forms a spherical linkage or joint because of the intersection of the two axes of rotation of the two revolute joints which substantially simplifies the joint output guidance problem for the controller because of the existence of closed form solutions to the equations expressing the position of positioner 75' as a function of the positions of shafts 62', 64' and 70'. However, the control of the two joints is complicated by their not being completely decoupled since the rotation of the first revolute joint formed by carrier 60' and clevis 55' forces gear 69' along gear 68' if the latter gear is held stationary by motor 81' thereby leading to an angular change of the second revolute joint formed by positioner 75' and carrier 60' unless countered by the controller if just the original rotational motion of the first revolute joint is desired. The range of possible rotation about the first and second revolute joints axes of rotation is, in each instance, less than a full circle because of interference from adjacent structures.

Figure 7A:
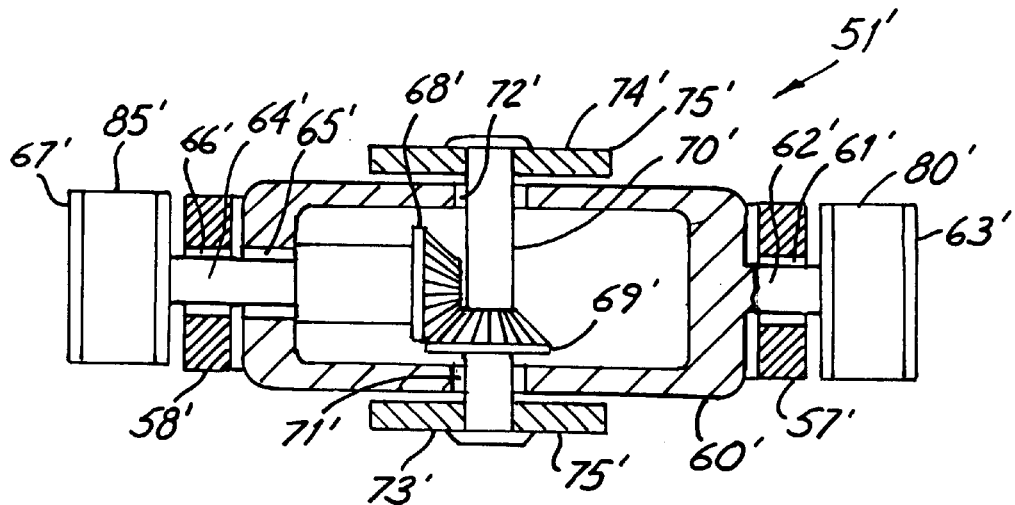
FIG. 7A shows a cross section view of a part of the structure shown FIG. 6
Figure 7B:
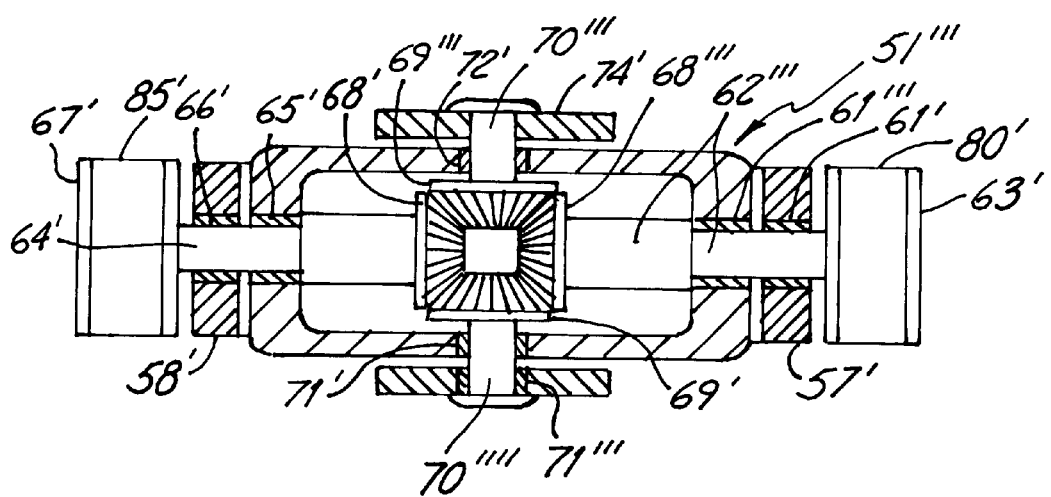
FIG. 7B shows an alternative structure in a cross section view.

An alternative positioning joint, 51''', using a differential gear arrangement is shown in FIG. 7B which, if operated on a differential basis, allows full decoupling. An extended version of shaft 62' of FIG. 7A, designated 62''', rotatably extends through clevis arm 57' and bushing 61' and also rotatably extends through the corresponding short side of rotatable bridge carrier 60' and a further bushing, 61''', to support on its end within the carrier a further bevel gear, 68''', across from bevel gear 68'. Also, shaft 70' is replaced by two shorter shafts, 70''' and 70'''', with shaft 70'''' now supporting on its end within bridge carrier 60' bevel gear 69' engaged with bevel gears 68' and 68'''. Shaft 70'''' is an idler shaft rotatably coupled to flange side 73' through a further bushing, 71'''. Shaft 70''' supports on its end within carrier 60' a further bevel gear, 69''', across from bevel gear 69' and also engaged with bevel gears 68' and 68'''. Rotating shafts 64' and 62''' in a common direction at a common speed rotates bridge carrier 60' and output positioner 75' together without rotating positioner 75' with respect to carrier 60', and allows greater torque to be supplied because or rotating both shafts together. Differentials in the rotation of these two shafts results in rotating positioner 75' with respect to carrier 60', but again possibly with greater torque such as if both shafts are rotated in opposite directions.

Returning to the configuration of FIG. 7A, rotation of carrier 60' about the first revolute joint axis of rotation is driven by an electrical motor, 76', (not seen in FIGS. 5, 6 and 7 though seen in a further figure introduced below) provided in motor housing 52'. Motor 76' has an output shaft connected to a speed reduction gearbox, 77', having an output shaft, 78', (not seen in FIGS. 5, 6 and 7 though seen in a further figure introduced below) affixed to a drive pulley, 79'. A drive belt, 80', couples drive pulley 79' to driven pulley 63' to enable motor 76' to rotate pulley 63' and shaft 62', and so carrier 60', over a selected angular range in the associated possible range of rotation under direction of the control system connected to motor 76' by wires provided as described above.

Similarly, rotation of positioner 75' about the second revolute joint axis of rotation is driven by an electrical motor, 81', provided in motor housing 54'. Motor 81' has an output shaft connected to a speed reduction gearbox, 82', having an output shaft, 83', affixed to a drive pulley, 84'. A drive belt, 85', couples drive pulley 84' to driven pulley 67' to enable motor 81' to rotate pulley 67' and shaft 64', and so positioner 75' through gears 68' and 69', over a selected angular range in the associated possible range of rotation under direction of the control system connected to motor 81' by wires provided as described above. Having the motors 76' and 81' positioned with their motor output shafts parallel to one another results in a structural configuration for positioning joint 51' that is relatively wide compared to its thickness to thereby simulate the relative dimensions of a human wrist.

Changing the ratio of diameters of drive pulleys 79' and 84' to the diameters of the their corresponding driven pulleys 63' and 67' does not significantly affect this configuration result but does allow trading torque and precise positioning for speed of angular change in the drive pulleys, or vice verse. A similar result occurs for changing the ratio of teeth in gears 68' and 69'.

Positioner 75' supports on the output support plate thereof, and thus selectively positions, an end manipulator, 90', for simulating a human hand and, to do so, has five further structures mounted thereon as part of end manipulator 90' with a small portion of each being seen in FIG. 6. A complete perspective view of end manipulator 90' taken from the side of positioner 75' having flange side 74' thereon is seen in FIG. 5.

Shown there is a human palm-like structure, 91', supported on two pedestals including a fixed pedestal, 92', that is fixedly attached to positioner 75' toward one end thereof by a base that is asymmetrical in being longer in the long direction of the support plate of positioner 75' parallel to flange sides 73' and 74' than it is wide where joined with the support plate of positioner 75', this base rising to a cantilevered support plate extending over the support plate of positioner 75' in its longer direction and extending parallel thereto. The other pedestal supporting palm-like structure 91' is a moveable pedestal, 93', in the form of a truncated cylinder where rotatably connected to the support plate of positioner 75' by the ball in a ball and socket joint, 94', with this support plate providing the socket at a location between the attachment of the base of pedestal 92' to the support plate of positioner 75' and the nearest end of that plate.

On the opposite end of the support plate of positioner 75' is provided a support ring, 95', mounted so that a plane including the perimeter of the ring is canted from a plane including the support plate of positioner 75' toward a direction opposite the direction flange sides 73' and 74' extend therefrom. A clevis, 96', generally shaped like clevis 55' described above is rotatably attached by its base to the support plate of positioner 75' adjacent to flange side 74' across from pedestal 92' and 93'. Finally, a wiring harness holder, 97', is attached to positioner 75' across flange side 73' to hold wiring for linear actuators used in the remainder of end manipulator 90'.

The cantilevered support plate of fixed pedestal 92' has rigidly affixed thereto two subpedestals, 98' and 99', each shaped as a truncated cylinder at its attachment point and along a portion of its extent. Subpedestals 98' and 99', and moveable pedestal 93', each extend through an opening in, and pass beyond, palm-like structure 91'. Palm-like structure 91' is formed of a flexible, polymeric material, and has thin linear regions in this polymeric material extending approximately parallel to the subpedestals that serve to segment it into three sections which can bend with respect to adjacent ones thereof along these linear regions. That is, these sections can bend back and forth relative to adjacent ones thereof about axes in a direction more or less parallel to the direction of extent of moveable pedestal 93' and of subpedestals 98 and 99'.

The opening in the section of palm-like structure 91' through which subpedestal 99' extend is located at the end of the cantilevered support plate of fixed pedestal 92' farthest from the base thereof, and is thus one of the outer sections of palm-like structure 91'. The opening in the other outer section of palm-like structure 91' through which moveable pedestal 93' extends is located at the opposite end of palm-like structure 91'. This leaves the remaining opening in palm-like structure 91' through which subpedestal 98' extends centered in the middle section between the two outer sections. The outer segment of palm-like structure 91' through which subpedestal 99' extends and a portion of the middle segment thereof abut the surface of the cantilevered support plate in fixed pedestal 92'.

This arrangement allows moveable pedestal 93', and the outer section of palm-like structure 91' through which it extends, to be moved with respect to the other two sections of palm-like structure 91' about ball and socket joint 94' and about the linear region separating this outer section from the middle section of palm-like structure 91'. The source of such movement is provided by a linear actuator, 100', having its base, 101', (which may contain a force sensor) rotatably connected in the openings in the ends of the arms of clevis 96'. The output shaft and outer body, 102', of linear actuator 100' is connected in a ball and socket joint, 103', in which the ball is provided at the end of output shaft 102' and the socket is provided attached to moveable pedestal 93' through a portion of the outer section of palm-like structure 91' through which moveable pedestal 93' extends. Thus, the control system indicated above which operates linear actuator 100' through wires (not shown) can cause output shaft 102' of that actuator to extend and retract to thereby cause moveable pedestal 93' at the location of the section of palm-like structure 91' through which it extends to move toward either side of the middle section of palm-like structure 91' about ball and socket joint 94' to provide akin to the squeezing together and moving apart of human palm portions.

At the ends of subpedestals 98' and 99' opposite the ends thereof affixed to the cantilevered support plate of fixed pedestal 92', and at the end of moveable pedestal 93' opposite the end with ball and socket joint 94', the cylindrical shaped portions of each serve as a clevis base and there beyond diverge into a pair of parallel arms with openings therein like clevis 55' above to form a corresponding one of three clevises, 105' A, 105' B, and 105' C Each of three shackles, 106' A, 106' B, and 106' C in the form of a base with two spaced apart parallel arms extending perpendicularly thereto with end openings to thereby resemble a U-shape, have that base thereof rotatably mounted between the arms of a corresponding one of devises 105' A, 105' B, and 105' C The long extent direction of a shackle base is perpendicular to the axis of rotation thereof extending through the openings in the arms of the corresponding clevis, an axis that is approximately perpendicular to the long extent direction of the support plate of positioner 75'. Each of these clevis and shackle pairs together form an open chain of two revolute joints (including the rotatable connection to the shackle arms in the openings therein to be described below) that serve as a universal joint.

Figures 8, 9:
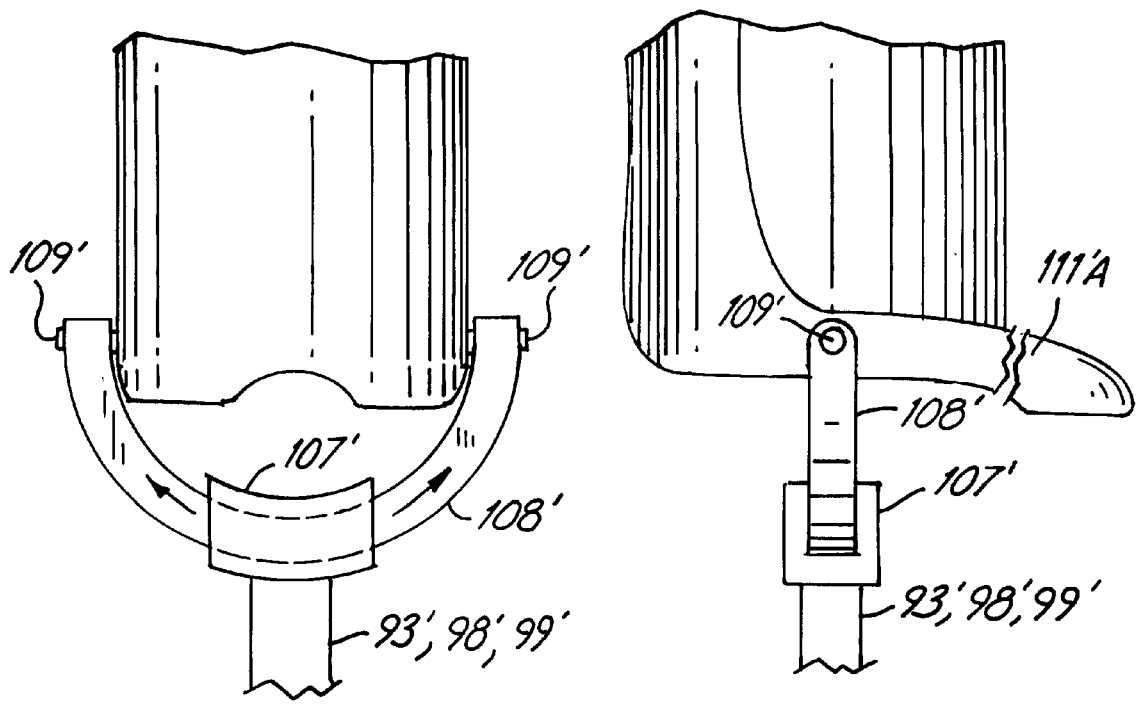
FIGS. 8 and 9 show side views of an alternative for portions of the structure shown in FIG. 5.

Alternatively, as shown in FIGS. 8 and 9, such a joint can be provided by having moveable pedestal 93', or subpedestals 98' and 99', or all of them, merge into a truncated, curved axis rectangular solid shell, 107', to thereby have a curved, rectangular cross-section slot therethrough. A rectangular cross-section slide, 108', having a axis symmetry following a semicircle is then inserted in this slot. Slide 108' has openings at each end thereof through which truncated cylindrical pins 109', can be inserted and attached to the structure that is to rotate on these pins.

The structures that are to rotate on pins 109', or in shackles 106' A, 106' B, and 106' C are shown in FIG. 5 rotatably attached to those shackles, and are a corresponding one of three more or less aligned effectors, 110' A, 110' B, 110' C, each of which forms a more or less planar linkage. However, because each of effectors 110' A, 110' B, 110' C can rotate about an axis extending between the arms of a corresponding one of shackles 106' A, 106' B, and 106' C and because shackles 106' A, 106' B, and 106' C can rotate about an axis extending between the arms of the corresponding one of devises 105' A, 105' B, and 105' C that is perpendicular to the corresponding axis of rotation of its effector rotatably held therein, effectors 110' A, 110' B and effectors 110' A, 110' B, 110' C 110' C, though planar linkages themselves, can also rotate side to side out of the linkage plane.

Figure 11:
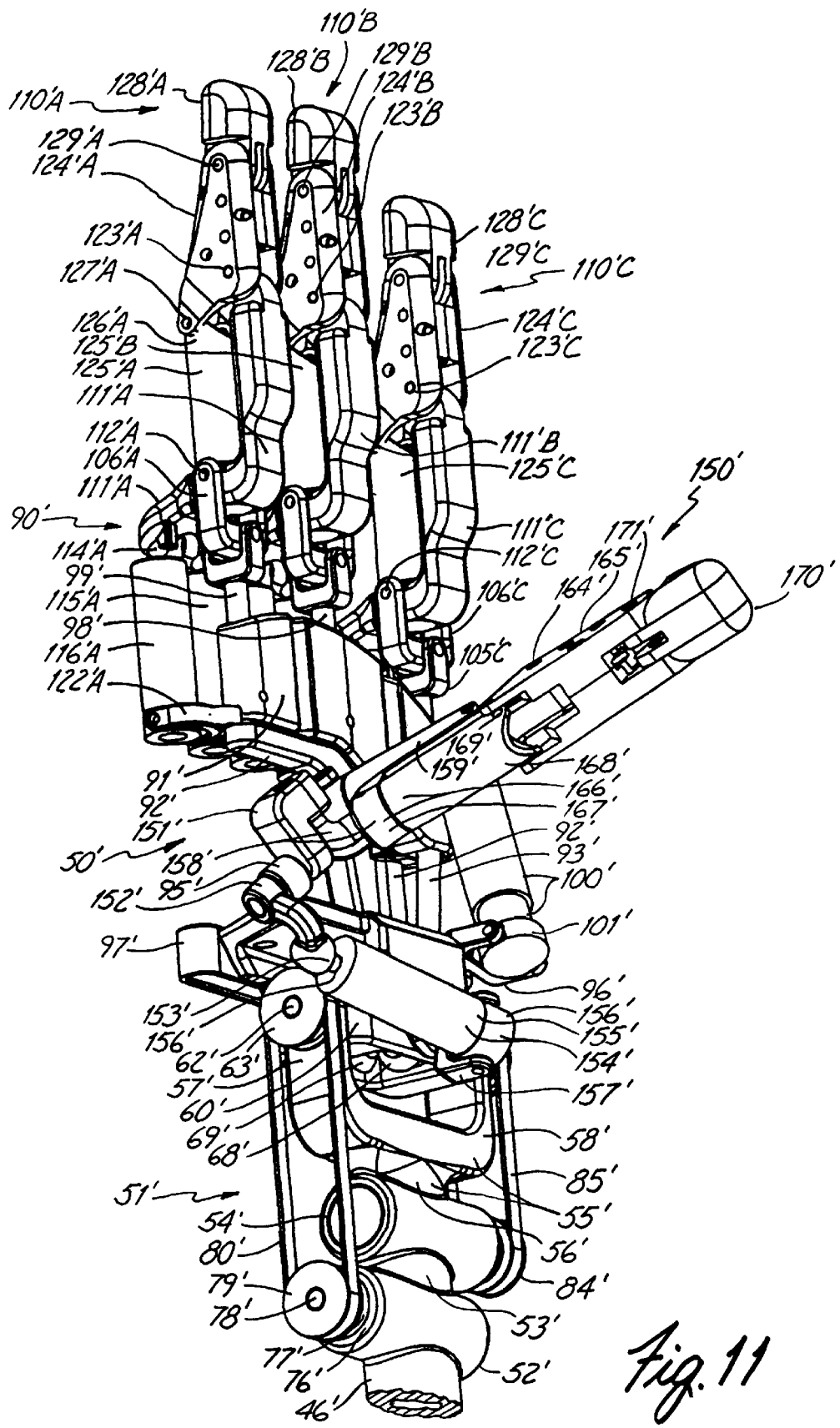
Figure 12:
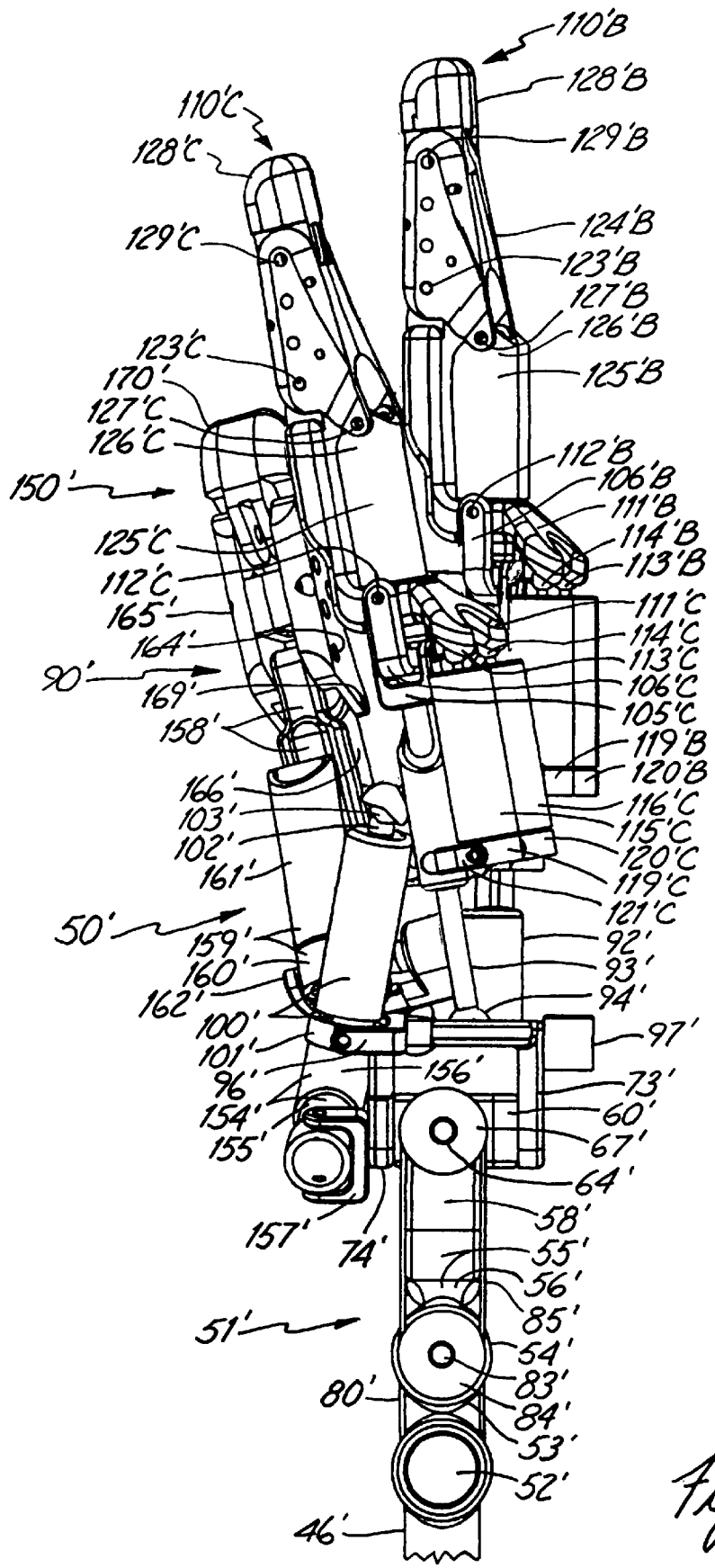
Figure 13:
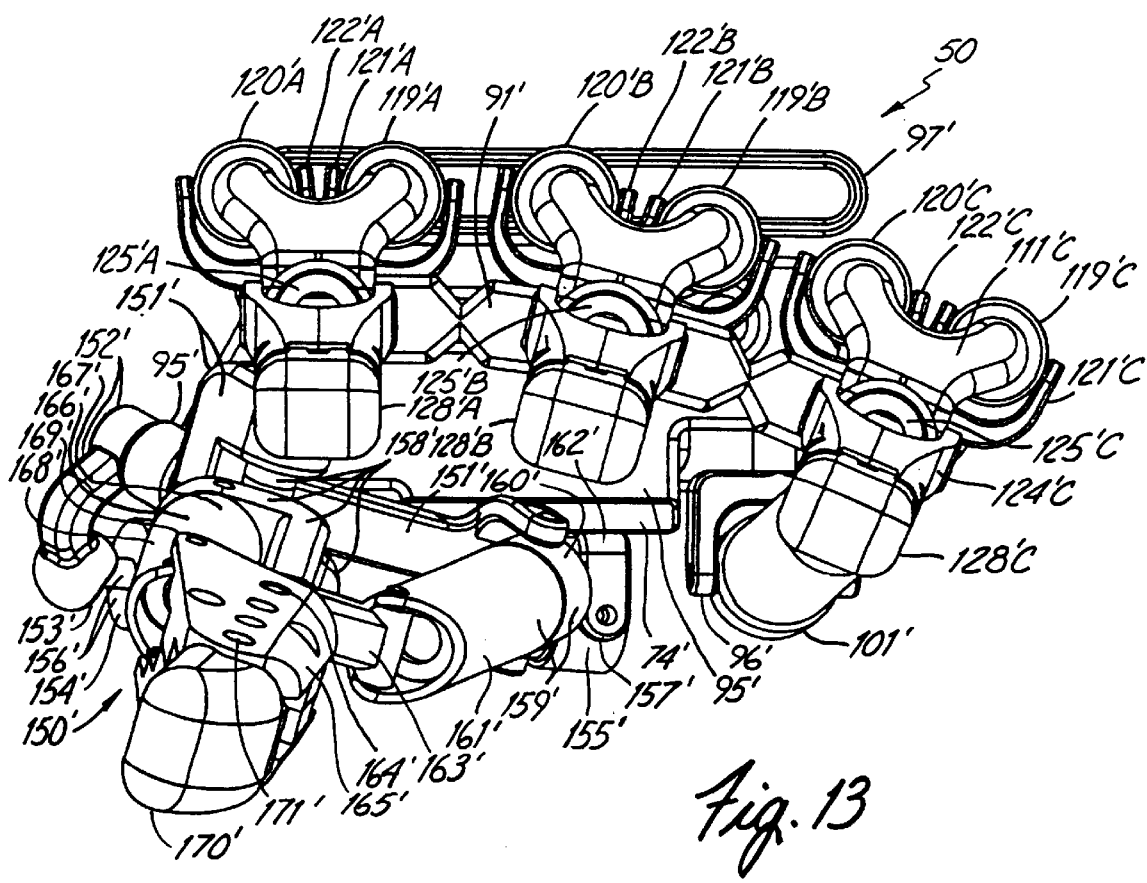

Each of these effectors has a corresponding one of three effector bases, 111' A, 111' B, 111' C Each of these effector bases has a plateau well pivot region which is rotatably connected by a corresponding one of three pin sets, 112' A, 112' B, 112' C, to the opening in the arms of a corresponding one of shackles 106' A, 106' B, and 106' C, i.e., on the other side of the corresponding one of the universal joints formed at the ends of moveable pedestal 93' and subpedestals 98' and 99'. Thus, the axis of rotation of each of these effectors extending through these pins is perpendicular to the primary direction of extent of the plateau in its plateau well pivot region direction. Extending more or less perpendicularly from one side of the plateau well pivot region of each of the base effectors along its direction of primary extent, and so perpendicularly to the axis of rotation through the corresponding one of these pin sets, is an extension support structure that nearby is curved in a right angle to be perpendicular to the direction of primary extent of that plateau well pivot region. Also extending from the plateau well pivot region on the other side thereof at an incline with respect to the direction of primary extent of that plateau well pivot region is an inclined dual wing drive structure. Some aspects of these can be better seen in FIG. 10A which provides a perspective view of the other side of joint and manipulator structure 50' from that shown in FIG. 5, in FIG. 11 which provides a perspective view of the same side of joint and manipulator structure 50' shown in FIG. 5 but from a different perspective, in FIG. 12 which provides a perspective view of the side of joint and manipulator structure 50', and in FIG. 13 which provides a perspective view of the top of joint and manipulator structure 50'.

Each of the two wings of the inclined dual wing drive structure of effector base 111' A is connected by a corresponding one of a pair of ball and socket joints, 113' A and 114' A, to one of a pair of linear actuators, 115' A and 116' A, at the corresponding one of the outer body and output shafts thereof, 117' A and 118' A. The sockets of ball and socket joints 113' A and 114' A are provided in a corresponding one of two wings in the inclined dual wing drive structure of effector base 111' A, and the balls are provided affixed to output shafts 117' A and 118' A. The bases, 119' A and 120' A, of linear actuators 115' A and 116' A, respectively, (each of which may contain a force sensor) are each rotatably connected in the openings in the ends of the arms of a corresponding one of a pair of clevises, 121' A and 122' A. Each of clevises 121' A and 122' A is shaped like clevis 55' described above, and each has its stem portion rotatably connected to the cantilevered support plate of fixed pedestal 92' on the side thereof shown in FIG. 10A.

Figure 10A:
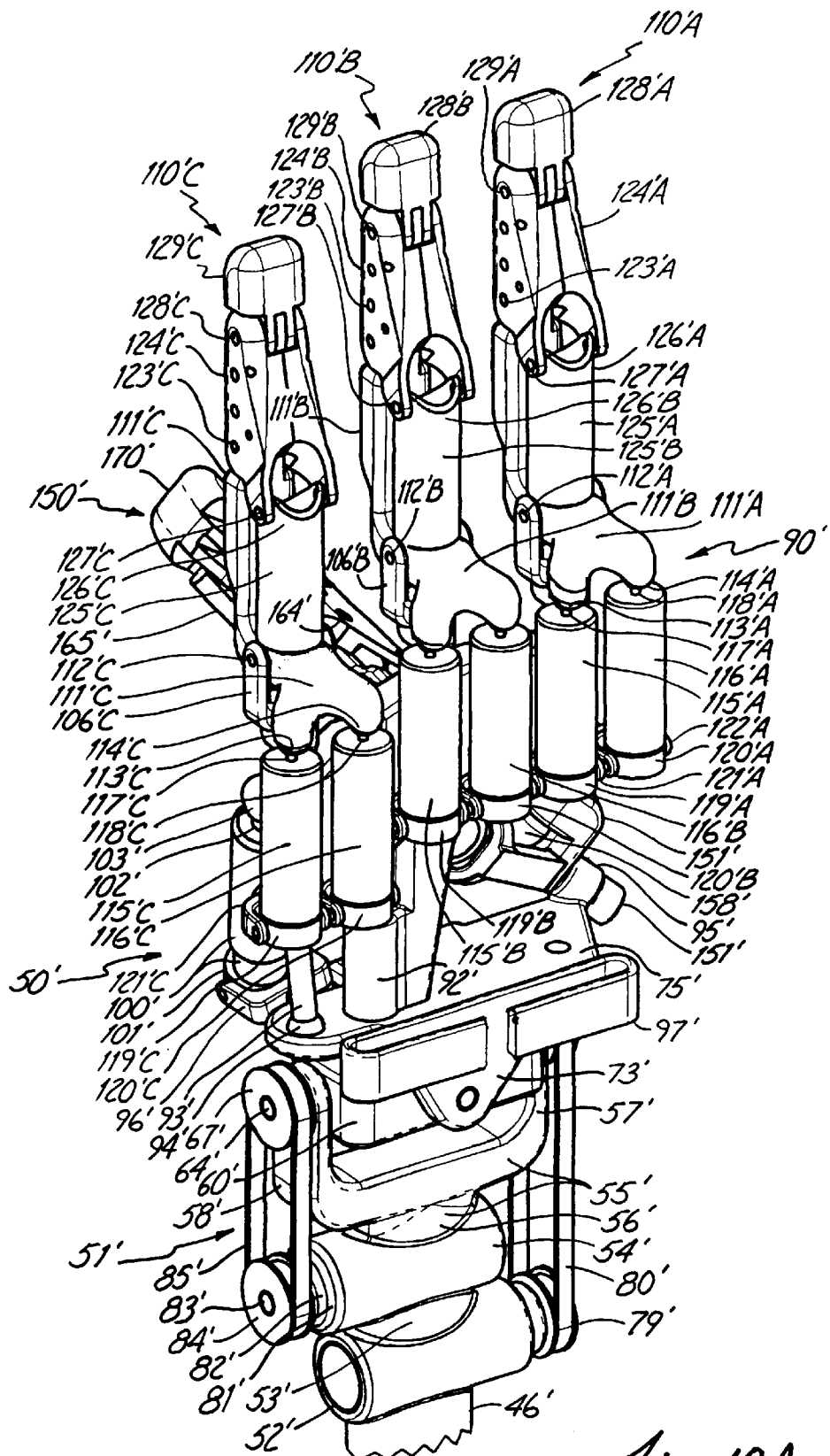
FIG. 10A shows an alternative perspective view of the structure shown in FIG. 5 and FIGS. 10B and 10C show side views of an alternative for portions of the structure shown in FIGS. 5 and 10A, FIGS. 11, 12 and 13 show alternative perspective views of the structure shown in FIGS. 5 and 10A.

In FIG. 10B, linear actuators, 115''' A and 116' A, are shown as alternatives to linear actuators 115' A and 116' A in FIG. 10A. Actuator 116''' A is shown moved around the edge of pedestal 92' to be partially in front of actuator 115''' A to thereby reduce the lateral extent of that actuator pair across pedestal 92' which aids in allowing another effector, 110' D, to be mounted on that pedestal. In addition, as shown for the example of actuator 15''' A in FIG. 10C that is similar to the other linear actuators shown in FIG. 10B, actuator 115''' A is held rigidly to prevent any translation rotation of the outer body thereof by the gripping arms of a clip, 115'''' A, that is mounted to pedestal 92' by a base provided at the joining point of those arms. An actuator output extension, 115' A, is formed with a threaded rod having a hexagonally faceted sphere-like end that is provided captured in a reduced opening recess in the end of the output member of actuator 115''' A as a ball and socket joint, and with a cylindrical nut with an interior thread also having a hexagonally faceted sphere-like end to be captured in a wing of the inclined dual wing drive structure of effector base 111' A to form ball and socket joint 113' A. Screwing this nut a suitable distance on the threaded rod allows adjusting the length of actuator output extension 115' A. The following description returns to the arrangement of FIG. 10A.

Thus, various combinations of extensions and retractions of output shafts 117' A and 118' A of the linear actuators 115' A and 116' A, respectively, causes the inclined dual wing drive structure of effector base 111' A to correspondingly rotate about its axis of rotation extending through pin set 112' A, and the inclined dual wing drive structure of effector base 111' A plus shackle 106' A to correspondingly rotate about the axis of rotation of shackle 106' A extending through the arms of clevis 105' A. That is, linear actuators 115' A and 116' A are capable of forcing effector base 111' A to any angle with respect to vertical within a limited angular range about the vertical in FIGS. 5, 10A, 11, 12 and 13 substantially followed by the extension support structure of effector base 111' A in the straight-up position thereof in those figures. Extending or retracting the moveable ends of actuators 115' A and 116' A in unison forces effector base 111' A toward one side or the other of palm-like structure 91' with the combined forces supplied by each actuator, while differentials in the motions between output shafts 117' A and 118' A of these actuators result in side-to-side motions of effector base 111' A plus shackle 106' A. As a result, combinations of such motions allow choosing any desired angle for effector base 111' A with respect to the above described vertical within a limited range. The angular range possible for effector base 111' A is clearly limited mechanically by interference between that effector and structures on the side of positioner 75' at which flange side 74' is provided, by the maximum excursions of output shafts 117' A and 118' of actuators 115' A and 116' A from the bases thereof, and by the locations of any adjacent effector bases and the location of an opposing effector base not yet described. Practically, however, the angular range limits for effector base 111' A will be established by operating controls provided in the controller with respect to actuators 115' A and 116' A to limit the excursions of output shafts 117' A and 118' thereof with respect to the corresponding base for the conditions expected to be encountered by effector base 111' A during operation thereof.

The extension support structure of effector base 111' A extending from the other side of the plateau well pivot region thereof has an opening at the far end of that structure through which a pivot pin, 123' A, is inserted to rotatably connect to effector base 111' A to a first gripping extension, 124' A. Extension 124' A has a clevis-like end with two extensions between which the end portion of the extension support structure of effector base 111' A is held by pivot pin 123' A extending therethrough and through the two extensions of clevis-like end of the extension.

A linear actuator, 125' A, has a base end thereof (unseen in these figures but which may contain a force sensor) affixed in the hole, or well, provided in the plateau of the plateau well pivot structure of effector base 111' A so that the end of this base extends past pivot pins 112' A as fitted into that well and so into the region between the arms of shackle 106' A. This positioning of the base of linear actuator 125' A down into this well thereby keeps relatively short the distance between the pivot point of effector base 111' A about the axis of rotation established by pins 112' A and the pivot point for first gripping extension 122' A about the rotation axis thereof determined by pins 123' A. The end of the moveable outer body, 126', of actuator 125' A is rotatably connected between a pair of extensions forming a yolk in first gripping extension 124' A by further pair of pivot pins, 127' A. Extensions and retractions of moveable outer body 126' of linear actuator 125' A forces first gripping extension 124' A to rotate about pins 123' A toward one side or the other of effector base 111' A, typically as part of a gripping process with respect some adjacent object in providing a further link in the open linkage chain simulating a human finger to increase the capture arc thereof established by its extent. As shown in FIG. 10B, an alternative linear actuator, 125''' A, can be used in place of linear actuator 125' A held by a clip to effector base 111' A.

A second gripping extension, 128' A, has a portion thereof rotatably connected to first gripping extension 124' A between portions thereof forming a further yoke by a pin, 129' A, fixed in these portions at the end of the first gripping extension opposite the end having a yoke connected to effector base 111' A. Pin 129' A also has a gear centrally mounted thereon. This gear is engaged with gears not seen in first gripping extension 124' A forcing second gripping extension 128' A to rotate with respect to first gripping extension 124' A when the latter is rotated with respect to effector base 111' A again typically to further a gripping process by adding another link in the chain to further increase the capture arc thereof.

The remaining effectors 110' B and 110' C in FIG. 10A are constructed similarly to, and are operated similarly to, effector 110' A. A description of the construction and operation for either of the remaining effectors 110' B and 110' C thus follows from the foregoing such descriptions for effector 110' A by substituting the corresponding one of the letters B or C for the letter A in the designations used in those descriptions of effector 110' A above. Similarly, the remaining effectors 110' B, 110' C and 110' D in FIG. 10B are constructed similarly to, and are operated similarly to, effector 110' A in that figure but with a positioning difference. Instead of having one base effector linear actuator in front of the other to reduce the lateral extent of the pair across the lateral extent of pedestal 92' as for linear actuators 115''' A and 116''' A, the other base effector linear actuator pairs, 115''' B and 116''' B, 115'' C and 116' C, and 115' D and 116''' D, alternate in distance away from the corresponding base effector connection points within a pair and from pair to pair. In doing so, they partially overlap along the directions to the base effectors so that the output ends of some of these linear actuators face in part the opposite ends of other ones of these actuators to thereby reduce the lateral extent of each pair and the lateral extents of the group of pairs thus allowing adding effector 110' D to those mounted on pedestal 92' to give a more complete and proportional simulation of a human hand.

Figure 14:
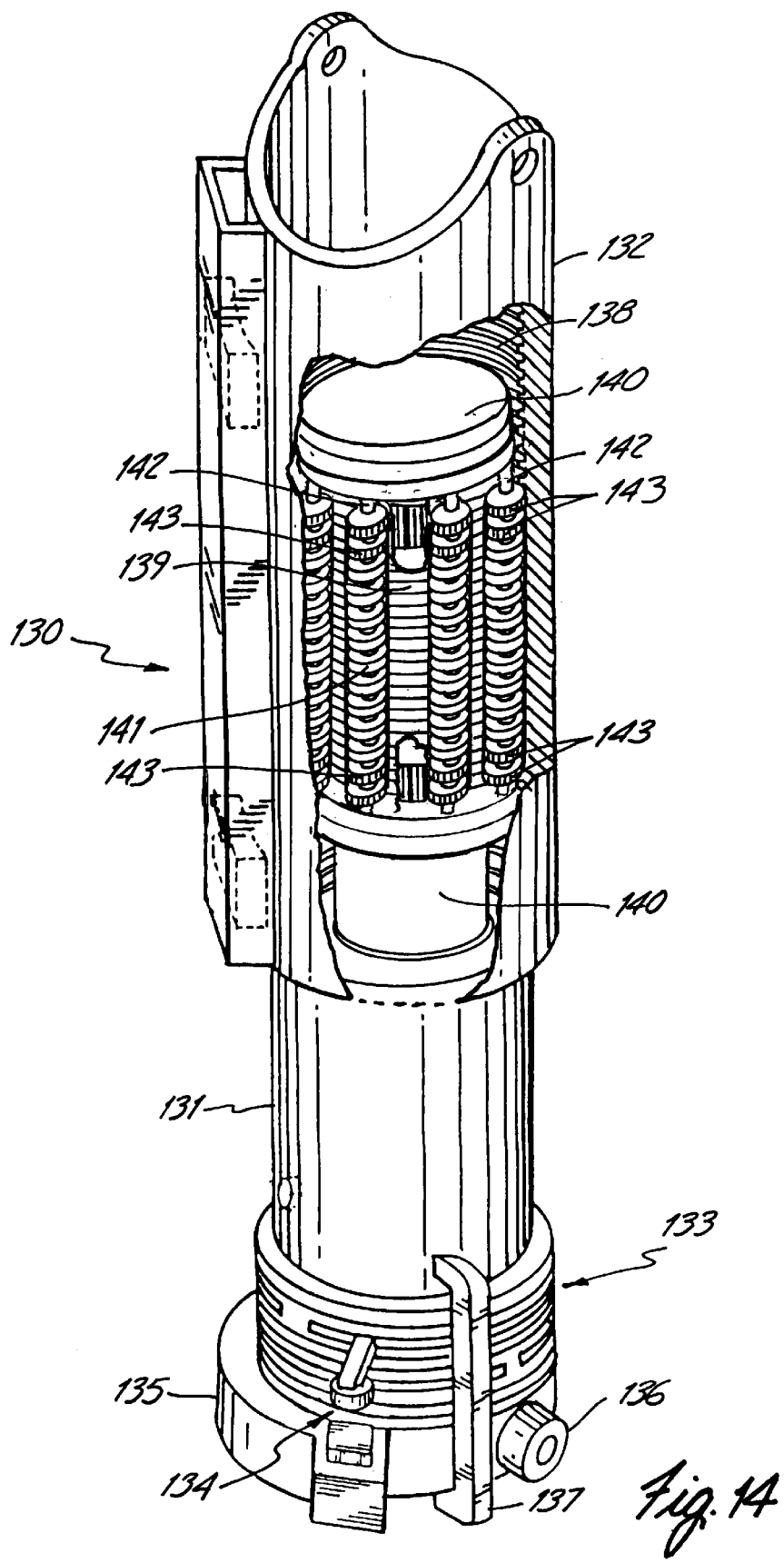
FIG. 14 shows a perspective view of portions of the structure shown in FIGS. 5, 10A, 11, 12 and 13.

FIG. 14 shows a perspective view of a linear actuator, 130, of the kind used in both joint and manipulator structure 50 and joint and manipulator structure 50' in FIGS. 5, 10A, 11, 12 and 13. Actuator 130 has a base, 131, more or less radially symmetric about a long axis of actuator 130 in the form approximately of a truncated cylindrical shell, and an outer body, 132, partially thereabout also in the form approximately of a truncated cylindrical shell more or less radially symmetric about the actuator long axis but of a larger interior diameter than the outer diameter of base 131. (Alternatively, outer body can additionally have an output shaft centered about the actuator long axis thereon, and affixed to, the end thereof rather than the openings across from one another at the end thereof as shown.) Base 131 has an unseen electric motor provided in its shell, and outer body 132 is driven by this motor to linearly extend or retract under the direction of the unseen control system, connected to the motor by unseen wiring, which determines when current is to be supplied to this motor to cause rotation in one direction or the other of its rotor.

Base 131 has a force sensor, 133, formed of a multiple slitted side truncated cylindrical resulting in partially separated rings that effectively become a spring that can be expanded or compressed by axial forces on actuator 130 that can be measured by measuring the resulting distances of expansion or compression. These distances measurements are made, for instance, using a magnet and a magnetic sensor pair, 134, mounted on force sensor 133 and on an actuator holder, 135, used for rotatably mounting actuator 130 typically in a clevis by a pair of pins, 136, protruding therefrom on opposite sides thereof. A limiter. 137, limits the expansion distance of force sensor 133.

Outer body 132 has spiral threading, 138, on its inner surface, and corresponding spiral threading, 139, is provided on a motor output shaft, 140, connected to the motor in base 131. Engaged with both threadings 138 and 139 are helical threads, 141, located at various radial positions between threadings 138 and 139 provided about a shaft, 142, having in common thereon a pair of gears, 143, mounted and affixed to the same shaft at each end of the helical thread thereon to maintain rotational phase with motor output shaft 140 having meshing gears thereon. The presence of the helical thread shafts between threadings 138 and 139 rather than these threadings being directly engaged with one another results in substantially reduced friction, speed reduction and reduced backlash.

A further effector, 150', and to a varying degree an opposing effector with respect to effectors 110' A, 110' B, 110' C described above, is provided as a human thumb-like effector and is mounted on positioner 75' using support ring 95'. Effector 150' is again a more or less planar linkage but, further, is provided to be specifically rotatable in a bushing provided in the opening in support ring 95'. Thus, a ring supported carrier, 151', has a cylindrical shaft extending through and past the opening of support ring 95' and the bushing therein.

On the side of support ring 95' facing in part the same direction as the side of the support plate of positioner 75' in facing bridge carrier 60', ring supported carrier 151' has, on the portion of the carrier cylindrical shaft extending past support ring 95', a crank arm, 152', affixed thereto with a clamping ring from which a bent shaft extends. The bent shaft at its other end is joined in a ball and socket joint, 153', connecting it with a linear actuator, 154', having a base, 155', (which may contain a force sensor) and an output shaft, 156'. Base 155' of linear actuator 154' is rotatably connected between the arms of a clevis, 157', like clevis 55' described above, having its base stem rotatably connected to flange side 74' of positioner 75'. A socket for ball and socket joint 153' is provided on the end of crank arm 152', and the ball is affixed to the output shaft 156' of linear actuator 154'. Wiring, not shown, connects linear actuator 154' to the controller for directing the operation thereof.

Carrier 151', considered on the opposite side of support ring 95', has as a part thereof, at the other end of the cylindrical shaft thereof extending through support ring 95', a base plate side of a right angle bracket affixed to that shaft end perpendicularly across the shaft axis of radial symmetry with this base plate side being shaped more or less as a rectangular solid. This right angle bracket has a further perpendicular plate side to form this bracket that extends at a right angle from an edge of the base plate side in a direction opposite to the carrier cylindrical shaft affixed to the base plate side as just described, this perpendicular plate side having an opening therein in which a bushing is positioned. The base plate side of the right angle bracket also has an inclined cantilevered plate extending from another side thereof adjacent to the perpendicular plate side at an angle to thereby be inclined partially in the direction of the perpendicular plate side and so in a direction opposite that from which the carrier of the cylindrical shaft extends from the base plate side but at an angle that is less than a right angle to the base plate side.

A gripping effector base, 158', has therein a cylindrical shaft portion which extends into a stub shaft by being bent to have a right angle with the axis of radial symmetry of the long part of the effector base cylindrical shaft portion. This stub shaft part is inserted in the bushing in the opening in the perpendicular plate side of the right angle bracket of carrier 151' so as to be rotatably connected thereto. The long axis of radial symmetry of the cylindrical shaft portion in the part thereof outside of the stub shaft in gripping effector base 158' intersects the inclined cantilevered plate of carrier 151'.

A linear actuator, 159', for rotating gripping effector base 158' about the axis of radial symmetry of the stub shaft thereof has a base, 160', (which may contain a force sensor) and an output body shell, 161'. Base 160' of linear actuator 159' is rotatably connected between the arms of a clevis, 162', like clevis 55' described above, extending from the far end of the inclined cantilevered plate of carrier 151'. Output body 161' of linear actuator 159' is rotatably connected to a drive beam, 163', affixed at right angles to gripping effector base 158' at a point approximately two-thirds the length of the long part of the cylindrical shaft portion of this effector base from the right angle bend leading to the stub shaft part thereof. Again, wiring, not shown, connects linear actuator 159' to the controller for directing the operation thereof.

Here, too, various combinations of extensions and retractions of output shaft 156' and output body 161' of the linear actuators 154' and 159', respectively, causes carrier 151' to correspondingly rotate, in the first instance, about its axis of rotation extending through its cylindrical shaft passing through support ring 95' to thereby include in that axis the axis of radial symmetry of that shaft, and, in the second instance, causes gripping effector base 158' to correspondingly rotate about its axis of rotation which is the axis of radial symmetry of the stub shaft in gripping effector base 158'. That is, linear actuator 154' is capable of forcing gripping effector base 158' to rotate in support ring 95' to face any one of aligned effectors 110' A, 110' B, 110' C to a selected degree under direction of the controller to thereby provide a selected gripping position arrangement between them, and linear actuator 159' is then capable under direction of the controller of forcing gripping effector base 158' toward or away from such an aligned effector or effectors, and their respective gripping extensions, so as to close or open the gap therebetween to thereby begin or end a gripping process about some object positioned therebetween.

The angular range possible for gripping effector base 158' is clearly limited mechanically by interference between that effector and palm-like structure 91' and structures supported thereby such as effectors 110' A, 110' B, 110' C, and by the maximum excursions of output shaft 156' and output body 161' of the linear actuators 154' and 159' from the bases thereof. Practically, again, however, the angular range limits for gripping effector base 158' will be established by operating controls provided in the controller with respect to actuators 154' and 159' to limit the excursions of output shaft 156' and output body 161' thereof with respect to the corresponding base for the conditions expected to be encountered by gripping effector base 158' during operation thereof.

The far end of the of the long part of the cylindrical shaft portion in gripping effector base 158' fits into a sleeve portion of an actuator holder in gripping effector base 158' which has an opening therein at the end of this sleeve portion past the end of the cylindrical shaft portion. Through this opening a pin, 164', is provided to rotatably connect a first gripping extension, 165', to gripping effector base 158'. A clevis-like end of first gripping extension 165' has two extensions between which the far end of the sleeve part of actuator holder in gripping effector base 158' is positioned to be held by pivot pin 164' extending through the opening therein and through the two extensions of clevis-like end of the extension.

A linear actuator, 166', has a base end, 167', thereof (which may contain a force sensor) affixed in an partial ring end of a holding bracket at the opposite end of the actuator holder in gripping effector base 158'. This holding bracket in actuator holder is formed by two arms extending from the sleeve portion thereof along much of the long part of the cylindrical shaft portion to the partial ring which is formed following a semicircular path extending from these two arms outwardly away from the cylindrical shaft portion. The end of a moveable outer body shell, 168', of actuator 166' is rotatably connected between a pair of extensions forming a yolk in first gripping extension 165' by further pair of pivot pins, 169'. Extensions and retractions of moveable outer body 168' force first gripping extension 165' to rotate forward and backward about pivot pin 164' with respect to gripping effector base 158' to permit further circumscription of an object between them and one or more of the aligned effector based open chains in gripping that object. Here too, wiring, not shown, connects linear actuator 166' to the controller for directing the operation thereof.

A second gripping extension, 170', has a portion thereof rotatably connected to first gripping extension 165' between two spaced apart, extended portions thereof forming a yoke by a pin, 171', fixed in these extended portions at the end of the first gripping extension opposite the clevis-like end of first gripping extension 166' connected to gripping effector base 158'. Pin 171' also has a gear centrally mounted thereon. This gear is engaged with gears not seen in first gripping extension 165' forcing second gripping extension 170' to rotate with respect to first gripping extension 165' when the latter is rotated with respect to gripping effector base 158', and again adds to the capture arc formed by the extent of them as an open linkage chain.

Again, as shown in FIG. 10B, linear actuators 154', 159' and 166' of FIGS. 5, 10A, 11, 12 and 13 can have alternative linear actuators like linear actuator 115'" A substituted therefor. Thus, linear actuators 154'", 159'" and 166'" are shown in FIG. 10B replacing linear actuators 154', 159' and 166' of FIGS. 5, 10A, 11, 12 and 13.

Returning to robot 40 of FIG. 2, a manipulator, 10C, like manipulator 10 of FIG. 1, supports the base of "tee" structure 41 in robot 40 in having this structure mounted on manipulable support 32C thereof. Mounting arrangement 11C, having one end thereof connected to base support 12C of manipulator 10C, has the other end connected to a rounded corner, triangular shaped surface of a triangular shaped support plate structure, 180, extending between two such triangular shaped surfaces, which thus supports the upper torsolike portion of robot 40. Linear actuators 15C and 16C are mounted on support pedestals 14C on mounting arrangement 11C and connected to the corresponding lower pivoting links which can cause manipulable support 32C of manipulator 10C, supporting "tee" 41 and the structures connected thereto including any head-like structure provided, to move to simulate selected bending motion of the human upper torso under direction of the controller. Supplementing linear actuators 15C and 16C are two further linear actuators, 35C and 37C, which are mounted on support pedestals 14C on mounting arrangement 11C and connected to the corresponding lower pivoting links just as are linear actuators 15C and 16C. These added linear actuators can, in addition to providing further force and stability, be operated antagonistically with the other linear actuators to thereby reduce backlash in the motion of manipulator 10C, and they allow manipulator 10C to more precisely position the upper torso-like portion of robot 40 under direction of the system controller after the leg-like portions thereof (to be described below) have been used to coarsely position that robot. Alternatively, additions 35C and 37C can, instead of being linear actuators, be shock absorbers to damp impulsive forces on manipulator 10C.

Triangular shaped support plate structure 180 has an angled bracket plate, 181, with a first plate portion fastened to a side of structure 180 extending perpendicularly to the triangular surface supporting mounting arrangement 11C across from a corner of that surface. A second plate portion of angle bracket plate 181 is more or less of a rectangular shape and bent from the first plate portion away from structure 180. A first side of second plate portion of angle bracket 181 approximately perpendicular to the bend in that plate, and on the left in viewing FIG. 2, has a manipulator, 10D, like manipulator 10 of FIG. 1, useful for simulating a human right hip, mounted thereto parallel to the long axis of mounting arrangement 11D of manipulator 10D between its connection to base support 12D (unseen in FIG. 2) and support pedestals 14D thereon. Linear actuators 35D and 37D (connected to lower pivoting links 20" D and 20'" D rather than to lower pivoting links 20D and 20' D in the manner of linear actuators 16 and 15 in FIG. 1 being connected to lower pivoting links 20 and 20' there) are mounted on support pedestals 14D on mounting arrangement 11D and connected to the corresponding lower pivoting links which can cause manipulable support 32D of manipulator 10D to move to simulate selected right human hip motion under direction of the controller.

Manipulable support 32D is connected to a bent upper leg bar, 182, which has at its opposite end a yoke, 183, in which a lower leg bar, 184, is rotatably connected by a pair of pin-like bosses, 185, each extending through a yoke arm opening to be affixed in the sides of the upper leg bar yoke thereby forming a single degree of freedom joint, 186, simulating a human knee. A linear actuator, 187, is connected between upper leg bar 182 and lower leg bar 184 to operate that joint by causing lower leg bar 184 to selectively rotate in yoke 183 about pin-like bosses 185. A motor and a rotational joint arrangement contained within upper leg bar 182 allows it to be rotated over an angular range with respect to manipulator 10D. A two degree of freedom joint, 190, simulating a human ankle, to which a foot-like structure, 191, is attached, is mounted on the end of lower leg bar 184, and a motor and a rotational joint arrangement contained within lower leg bar 184 allows two degree of freedom joint 190 together with foot-like structure 191 to be rotated over an angular range with respect to lower leg bar 184.

Similarly, a second side of second plate portion of angle bracket 181 at a shallow acute angle with, but primarily parallel to, the first side to also be approximately perpendicular to the bend in that plate, and on the right in viewing FIG. 2, has a manipulator, 10E, like manipulator 10 of FIG. 1, useful for simulating a human left hip, mounted thereto parallel to the long axis of mounting arrangement 11E of manipulator 10E between its connection to base support 12E and support pedestals 14E thereon (not seen in FIG. 2). Linear actuators 15E and 16E (not all seen in FIG. 2) are mounted on support pedestals 14E on mounting arrangement 11E and connected to the corresponding lower pivoting links which can cause manipulable support 32E of manipulator 10E to move to simulate selected right human hip motion under direction of the controller.

Manipulable support 32E is connected to a bent upper leg bar, 182', which has at its opposite end a yoke, 183', in which a lower leg bar, 184', is rotatably connected by a pair of pin-like bosses, 185', each extending through a yoke arm opening to be affixed in the sides of the upper leg bar yoke thereby forming a single degree of freedom joint, 186', simulating a human knee. A linear actuator, 187', is connected between upper leg bar 182' and lower leg bar 184' to operate that joint by causing lower leg bar 184' to selectively rotate in yoke 183' about pin-like bosses 185'. A two degree of freedom joint, 190', simulating a human ankle, to which a foot-like structure, 191', is attached, is mounted on the end of lower leg bar 184', and a motor and a rotational joint arrangement contained within lower leg bar 184' allows two degree of freedom joint 190' together with foot-like structure 191' to be rotated over an angular range with respect to lower leg bar 184'.

Figure 15:
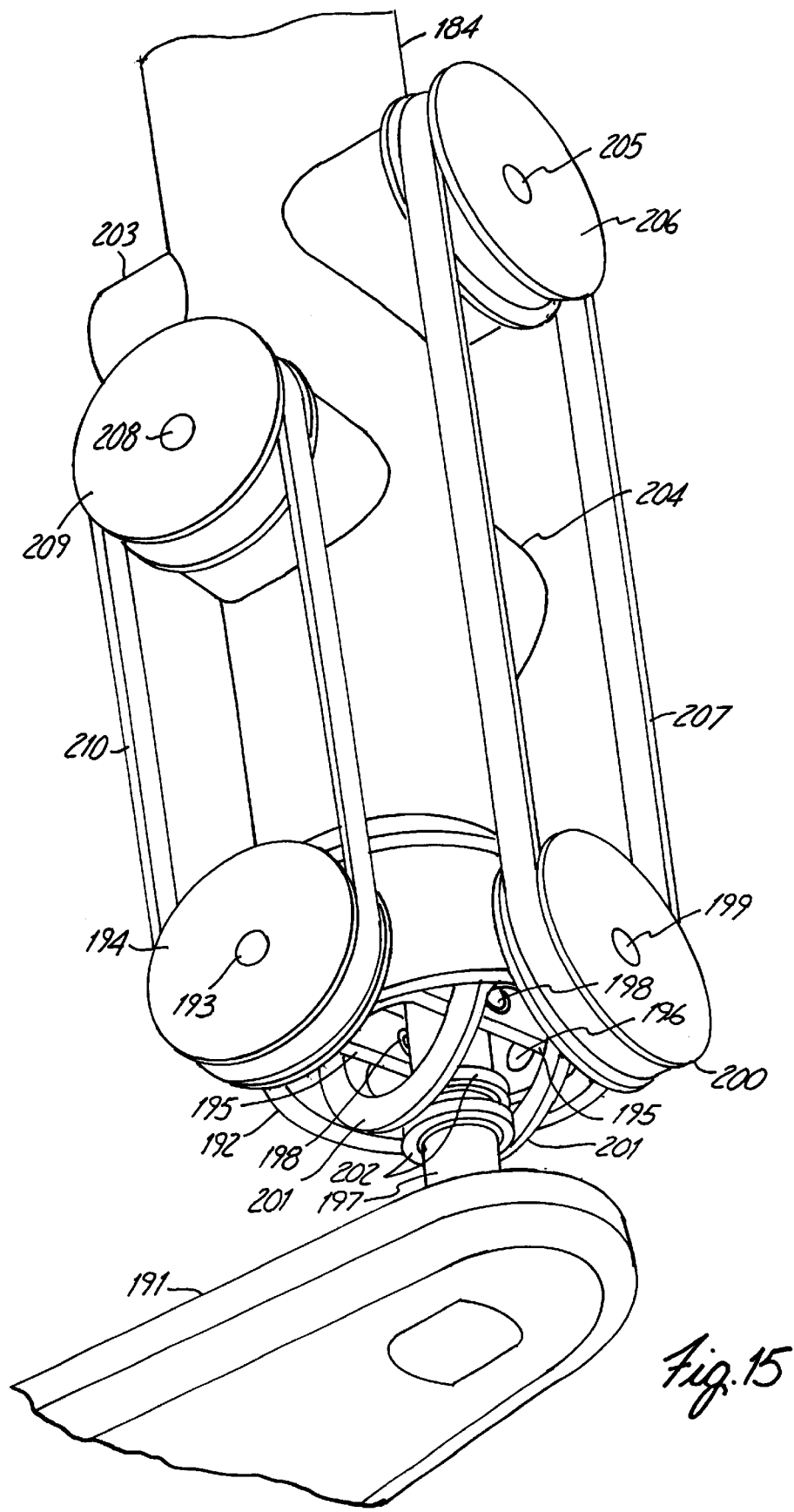
FIG. 15 shows a perspective view of a portion of the structure shown in FIG. 2.

Two degree of freedom joints 190 and 190' are shown to be identical in FIG. 2, and shown in greater detail in FIG. 15. Joint 190 will be described with structures in joint 190' mounted on the end of lower leg bar 184' identical to those in joint 190 mounted on the end of lower leg bar 184 having the same numerical designations there as they do in joint 190 but with a following prime mark.

Joint 190 has, as seen in FIGS. 2 and 15, a flared housing, 192, formed as a truncated cone shell portion having its small diameter end fastened about lower leg bar 184 and its large diameter end joined to a truncated cylindrical shell portion which has an open end at the end thereof opposite to its end joined to the truncated cone shell portion. A circular joint housing ring, unseen in FIGS. 2 and 15, also formed as a truncated cylindrical shell, is mounted on the inner periphery of the cylindrical shell portion of housing 192 inward from its open end. This housing ring has the shell thereof extended into four bosses parallel to the axis of radial symmetry at four locations 90° apart on this ring with each boss having an opening therein in which a bushing is provided. A pair of openings, unseen in FIGS. 2 and 15, is provided in the truncated cylindrical shell of housing 192 each across from, and axially aligned with, a corresponding one of two adjacent ones of these ring boss openings.

A shaft, 193, formed as a truncated cylinder, having a pulley, 194, affixed to an outer end thereof, extends from pulley 194 through one of the pair of housing truncated cylindrical shell openings and through the bushing in the ring boss opening across therefrom to be joined at its end to an output carrier, 195, extending between this ring boss opening and the ring boss opening opposite thereto on the other side of the ring housing. A shaft, 196, formed as a truncated cylinder, is affixed to the opposite end of output carrier 195 from the end thereof affixed to shaft 193 which extends into the bushing in this opposite side ring boss opening so that output carrier 195 is rotatably supported by the housing ring in opposite side ring boss openings thereof on shafts 193 and 196 to have an axis of rotation which includes the axes of radial symmetry of these shafts.

Output carrier 195 is formed as a closed loop metal strap with two rectangular plate long sides joined at the ends thereof by two curved plate short sides therebetween to which shafts 193 and 196 are affixed, thus leaving an open interior for the carrier between the long sides and the short sides accessible from both open sides of the closed strap loop. An output bar, 197, formed as a truncated cylinder, has one end thereof positioned within the interior of the closed strap loop of output carrier 195 and rotatably connected thereto by a pin, 198, extending through this output shaft and through bushings in each of two openings each of which is centered in one of the long sides of the closed strap loop of output carrier 195. The other end of output bar 197 is affixed to foot-like structure 191.

A further shaft, 199, formed as a truncated cylinder, having a pulley, 200, affixed to an outer end thereof, extends from pulley 199 through one of the pair of housing truncated cylindrical shell openings and through the bushing in the ring boss opening across therefrom to be joined at its end to a joined double bail, 201, extending between this ring boss opening and the ring boss opening opposite thereto on the other side of the ring housing. A shaft, unseen in FIGS. 2 and 15, formed as a truncated cylinder, is affixed to the opposite end of joined double bail 201 from the end thereof affixed to shaft 199 which extends into the bushing in this opposite side ring boss opening so that output carrier joined double bail 201 is rotatably supported by the housing ring in opposite side ring boss openings thereof on shaft 199 and the unseen shaft on its opposite side to have an axis of rotation which includes the axes of radial symmetry of these shafts.

Joined double bail 201 is formed as two spaced apart, parallelly oriented half rings that a rejoined to one another at the half ring ends by two curved plate short sides therebetween to which shafts 199 and the unseen attached shaft are affixed, thus leaving an open interior between the half rings and the short sides. The end of output bar 197 affixed to foot-like structure 191 is positioned to extend through this joined double bail interior opening in extending between its rotatable connection to output carrier 195 and its point of attachment to foot-like structure 191. A pair of relatively low friction sliding rings, 202, are positioned about output bar 197 to be between that output bar and the half rings of joined double bail 201 to permit these rings to guide motion of output bar 197 in its sliding back and forth therebetween. Thus, the rotation of pulley 194 and shaft 193 to rotate output carrier 195 results in rotation of output bar 197 perpendicular to the axis of rotation of output carrier 195 for any angle of joined double bail 201 set by the rotation of joined double bail 201 resulting from the rotation of pulley 200 and shaft 199.

A truncated cylindrical shell shaped motor housing, 203, is affixed in and through leg bar 184 with its axis of radial symmetry oriented perpendicular to the long axis of leg bar 184 and parallel to the axis of radial symmetry of shaft 199. Motor housing 203 has the end thereof on the side of leg bar 184 on which pulley 200 is positioned open to receive an electrical motor therein with the other end typically closed.

Another truncated cylindrical shell shaped motor housing, 204, is affixed in and through leg bar 184 closer to foot-like structure 191 with its axis of radial symmetry oriented perpendicular to that of motor housing 203 and to the long axis of leg bar 184, but parallel to the axis of radial symmetry of shaft 193. Motor housing 204 has the end thereof on the side of leg bar 184 on which pulley 194 is positioned open to receive an electrical motor therein, and typically, again, the other end of motor housing 204 is closed.

Leg bar 184 typically has an opening extending therethrough to allow control wiring to be installed. Motor housing 203, in addition to having some of such wiring terminate there for the motor to be provided therein, also has sufficient space therein to allow such wiring to pass from leg bar 184 to reach motor housing 204 for the motor to be provided there. Additional wiring, or other facilitating means, may also be passed through such openings and spaces if needed.

Rotation of joined double bail 201 about its axis of rotation is driven by an electrical motor, unseen in FIGS. 2 and 15, provided in motor housing 203. This motor has an output shaft connected to a speed reduction gearbox, unseen in FIGS. 2 and 15, having an output shaft, 205, affixed to a drive pulley, 206. A drive belt, 207, couples drive pulley 206 to driven pulley 200 to enable the motor in housing 203 to rotate pulley 200 and shaft 199, and so joined double bail 201, over a selected angular range in the associated possible range of rotation under direction of the control system connected to the motor in housing 203 by wires provided as described above.

Similarly, rotation of output carrier 195 about its axis of rotation is driven by an electrical motor, unseen in FIGS. 2 and 15, provided in motor housing 204. This motor has an output shaft connected to a speed reduction gearbox, unseen in FIGS. 2 and 15, having an output shaft, 208, affixed to a drive pulley, 209. A drive belt, 210, couples drive pulley 209 to driven pulley 194 to enable the motor in motor housing 204 to rotate driven pulley 194 and shaft 193, and so output carrier 195 over a selected angular range in the associated possible range of rotation under direction of the control system connected to the motor in housing 204 by wires provided as described above.

Although the present invention has been described with reference to preferred embodiments, workers skilled in the art will recognize that changes may be made in form and detail without departing from the spirit and scope of the invention.

What is claimed is:

1. A controlled relative motion system having first and second support structures with said first support structure having a first support offset structure extending along a first axis and said second support structure having a second support offset structure extending along a second axis, said system comprising:

an intermediate joint having a base member and a controlled position member that has an output carrier which can be angularly positioned with respect to said base member anywhere over a selected spatial surface, said intermediate joint base being affixed to an interior end of a selected one of said first and second support offset structures with said output carrier affixed to an interior end of that one remaining;

a first support joint having a base member supported by and affixed with respect to said first support offset structure at an exterior end thereof opposite said interior end thereof along said first axis and further having a controlled position member that has an output carrier which can be angularly positioned with respect to said base member anywhere over a selected spatial surface; and a second support joint having a base member supported by and affixed with respect to said second support offset structure at an exterior end thereof opposite said interior end thereof along said second axis and further having a controlled position member that has an output carrier which can be angularly positioned with respect to said base member anywhere over a selected spatial surface.

2. The system of claim 1 further comprising having said first support joint supported by and affixed with respect to said first support offset structure at an exterior end thereof through a first support holder structure affixed to said first support offset structure at said exterior end thereof at a location in said first support holder structure intersected by said first axis that is intermediate to two spaced apart holders in said first support holder structure to one of which said first support joint base member is affixed, and with a base member of a first supplemental support joint affixed to that remaining holder, said first supplemental support joint further comprising a controlled position member that has an output carrier which can be angularly positioned with respect to said base member anywhere over a selected spatial surface.

3. The system of claim 1 further comprising having said second support joint supported by and affixed with respect to said second support offset structure at an exterior end thereof through a second support holder structure affixed to said second support offset structure at said exterior end thereof at a location in said second support holder structure intersected by said second axis that is intermediate to two spaced apart holders in said second support holder structure to one of which said second support joint base member is affixed, and with a base member of a second supplemental support joint affixed to that remaining holder, said second supplemental support joint further comprising a controlled position member that has an output carrier which can be angularly positioned with respect to said base member anywhere over a selected spatial surface.

4. The system of claim 2 wherein said first support joint, with said output carrier of said first support joint controlled position member maximally spaced apart from said first support joint base member, defines a first support joint extension axis through said first support joint base member and said first support joint output carrier, and wherein said first supplemental support joint, with said output carrier of said first supplemental support joint controlled position member maximally spaced apart from said first supplemental support joint base member, defines a first supplemental support joint extension axis through said first supplemental support joint base member and said first supplemental support joint output carrier, said first support joint extension axis and said first supplemental support joint extension axes being nonparallel.

5. The system of claim 2 further comprising having said second support joint supported by and affixed with respect to said second support offset structure at an exterior end thereof through a second support holder structure affixed to said second support offset structure at said exterior end thereof at a location in said second support holder structure intersected by said second axis that is intermediate to two spaced apart holders in said second support holder structure to one of which said second support joint base member is affixed, and with a base member of a second supplemental support joint affixed to that remaining holder, said second supplemental support joint further comprising a controlled position member that has an output carrier which can be angularly positioned with respect to said base member anywhere over a selected spatial surface.

6. The system of claim 3 wherein said second support joint, with said output carrier of said second support joint controlled position member maximally spaced apart from said second support joint base member, defines a second support joint extension axis through said second support joint base member and said second support joint output carrier, and wherein said second supplemental support joint, with said output carrier of said second supplemental support joint controlled position member maximally spaced apart from said second supplemental support joint base member, defines a second supplemental support joint extension axis through said second supplemental support joint base member and said second supplemental support joint output carrier, said second support joint extension axis and said second supplemental support joint extension axes at least partly extending along said second axis.

7. The system of claim 5 wherein said intermediate joint, said first support joint, said first supplemental support joint, said second support joint and said second supplemental support joint further comprise at least one pivot holder comprising at least one member, an initial plurality of pivoting links each rotatably connected at one end thereof to a said pivot holder and rotatably connected at an opposite end thereof to said base member thereof and a subsequent plurality of pivoting links each rotatably connected at one end thereof to a said pivot holder and rotatably connected at an opposite end thereof to said output carrier thereof.

8. The system of claim 7 wherein each one of several pluralities of force imparting members is coupled to a corresponding one of said intermediate joint, said first support joint, said first supplemental support joint, said second support joint and said second supplemental support joint with each said force imparting means in a said plurality thereof provided for said corresponding joint being coupled to a an initial pivot link in said plurality thereof for said corresponding joint so as to be able to impart a force thereto to cause at least one of said initial plurality of pivoting links for said corresponding joint to rotate about an axis therethrough.

9. The system of claim 8 wherein said first support joint, said first supplemental support joint, said second support joint and said second supplemental support joint have said output carriers thereof each coupled through an extension member to a base member of a corresponding further joint having a controlled position member with an output carrier which can be selectively positioned with respect to said base member thereof, and with said extension member being rotatable with respect to that output carrier coupled thereto.

10. The system of claim 9 further comprising at least one of said further joints has said output carrier thereof coupled through a subsequent extension member to a base member of a corresponding terminating joint having a pair of slotted members rotatably coupled to said subsequent extension to each be capable of rotating about a corresponding one of a pair of axes substantially perpendicular to one another with a slot in each of said slotted members extending along said corresponding rotation axis thereof, said terminating joint further having an output carrier extending at least in part through said slot in each of said slotted members and a pair of force imparting means each coupled to a corresponding one of said slotted members to be capable of causing rotation thereof about said rotation axis corresponding thereto.

11. An articulated manipulating system for mounting on a base in a robotic manipulator and capable of engaging selected objects, said system comprising:

a subbase rotatably mounted on said base to have a single subbase rotation axis therethrough;

a first linear actuator coupled at one end thereof to said base and coupled at an opposite end thereof to said subbase to be capable of rotating said subbase about said subbase rotation axis;

a first effector base rotatably connected to said subbase to have a first effector rotation axis;

a second linear actuator coupled at one end thereof to said subbase and coupled at an opposite end thereof to said first effector base to be capable of rotating said first effector base about said first effector rotation axis.

12. The system of claim 10 further comprising a shackle having a pair of arms spaced apart by a recess space which arms are joined in a joining bar on one side of said recess space, an effector base rotatably mounted at a pivot location thereof to and between said spaced apart arms of the shackle so as to leave a recess space between an end of that said effector base rotatably mounted to said shackle and said joining bar thereof, a pedestal affixed to said base relatively near to where said subbase is rotatably mounted on said base and having said joining bar of said shackle rotatably coupled thereto, a gripping extension rotatably coupled to said effector base at an extension coupling location thereof spaced apart from said pivot location thereof, an extension linear actuator positioned adjacent to said effector base and coupled at one end thereof so as to have that end positioned at least in part in said recess space of said shackle with that remaining end of said linear actuator rotatably coupled to that said gripping extension, and a pair of effector linear actuators each having an end thereof connected to said base at corresponding base connection locations thereon, and each having that opposite end thereof rotatably connected to a said effector base at corresponding effector connection locations thereon so that any substantial differentials in movement of these actuators cause corresponding substantial motions of said effector base towards a corresponding one of said base connection locations and so that substantial common movements of these actuators causes substantial motions of said effector base toward or away from both of said base connection locations.

13. The system of claim 12 wherein said extension linear actuator has said one end thereof coupled to said effector base.

14. An articulated manipulating system for mounting on a base in a robotic manipulator and capable of engaging selected objects, said system comprising:

a plurality of shackles each having a pair of arms spaced apart by a recess space with said arms being joined in a joining structure on one side of said recess space;

a plurality of effector bases each rotatably mounted at a pivot location thereof to and between said separated arms of a corresponding shackle so as to leave a recess space between an end of that said effector base rotatably mounted to said shackle and said joining structure thereof;

a fixed pedestal affixed to said base and having said joining structure of a corresponding one of said plurality of shackles rotatably coupled thereto;

a moveable pedestal rotatably connected to said base and having said joining structure of a corresponding one of said plurality of shackles rotatably coupled thereto; and a pedestal linear actuator coupled at one end thereof to said base and coupled at an opposite end thereof to said moveable pedestal to be capable of rotating said moveable pedestal with respect to said base.

15. The system of claim 14 further comprising a plurality of gripping extensions each rotatably coupled to a corresponding one of said plurality of effector bases at an extension coupling location thereof spaced apart from said pivot location thereof, and a plurality of extension linear actuators each positioned adjacent to a corresponding one of said plurality of effector bases and each coupled at one end thereof so as to have that end positioned at least in part in said recess space of said shackle to which said corresponding effector base is rotatably coupled with that remaining end of said linear actuator rotatably coupled to that said gripping extension rotatably coupled to said corresponding effector base.

16. The system of claim 14 further comprising a pair of effector linear actuators each having an end thereof connected to said base at corresponding base connection locations thereon, and each having that opposite end thereof rotatably connected to a corresponding common one of said plurality of effector bases at corresponding effector connection locations thereon separated from said extension coupling location thereof by said pivot location so that any substantial differentials in movement of these actuators cause corresponding substantial motions of said corresponding effector base towards a corresponding one of said base connection locations and so that substantial common movements of these actuators causes substantial motions of said effector base toward or away from both of said base connection locations.

17. The system of claim 15 wherein each of said extension linear actuators in said plurality thereof has said one end thereof coupled to said corresponding effector base.

18. The system of claim 15 further comprising a pair of effector linear actuators each having an end thereof connected to said base at corresponding base connection locations thereon, and each having that opposite end thereof rotatably connected to a corresponding common one of said plurality of effector bases at corresponding effector connection locations thereon separated from said extension coupling location thereof by said pivot location so that any substantial differentials in movement of these actuators cause corresponding substantial motions of said corresponding effector base towards a corresponding one of said base connection locations and so that substantial common movements of these actuators causes substantial motions of said effector base toward or away from both of said base connection locations.

19. The system of claim 16 wherein one of said pair of effector linear actuators has said end thereof connected to said base so as to face a portion of that said opposite end of that remaining one of said pair of effector linear actuators in said pair of effector linear actuators each having that said opposite end thereof rotatably connected to said corresponding common one of said plurality of effector bases at corresponding effector connection locations thereon.

20. A controlled relative motion system having a base mounted in a robotic manipulator, said system comprising:

an extended open interior member being rotatably coupled to said base to be capable of rotating about a corresponding interior member rotation axis along which a pair of spaced apart interior member sides extend so as to have an extended space therebetween, said extended open interior member being rotatably coupled to said base at an end thereof joining said interior member sides at one end of said extended space by a first shaft coupled thereto and being rotatably coupled to said base at an opposite end thereof also joining said interior member sides at an opposite end of said extended space by a second shaft coupled thereto;

an output carrier having a pair of output carrier sides spaced apart by a recess space with said output carrier sides being joined in a joining structure on one side of said recess space, said output carrier being positioned to have said extended open interior member in said recess space with said output carrier sides at least in part extending substantially parallel to said interior member sides and to being rotatably coupled to said extended open interior member to be capable of rotating about a corresponding output carrier rotation axis substantially perpendicular to said interior member rotation axis, said output carrier being rotatably coupled to said extended open interior member by a follower shaft affixed to said output carrier and rotatably coupled to said extended open interior member;

an interior member first bevel gear located in said extended space and affixed to said first shaft;

an output carrier first bevel gear located in said extended space and affixed to said follower shaft to be engaged with said interior member first bevel gear; and a plurality of force imparting means mounted in said base with each of said first and second shafts being rotatably coupled to a corresponding one of said force imparting means in said plurality thereof.

21. The system of claim 18 wherein said second shaft is fixedly coupled to said extended open interior member at said opposite end thereof, and said follower shaft is rotatably coupled to said extended open interior member by passing through and being rotatably coupled to both said interior member sides and is affixed to both said output carrier sides.

22. The system of claim 18 wherein said second shaft is rotatably coupled to said extended open interior member at said opposite end thereof and further comprising said output carrier being also rotatably coupled to said extended open interior member by a gear shaft rotatably coupled to both said output carrier and to said extended open interior member, an interior member second bevel gear located in said extended space and affixed to said second shaft to be engaged with said output carrier first bevel gear, and an output carrier second bevel gear located in said extended space and affixed to said gear shaft to be engaged with said interior member first and second bevel gears.

* * * * *

UNITED STATES PATENT AND TRADEMARK OFFICE
CERTIFICATE OF CORRECTION

PATENT NO. : 6,658,962 B1
DATED : December 9, 2003
INVENTOR(S) : Mark E. Rosheim It is certified that error appears in the above-identified patent and that said Letters Patent is hereby corrected as shown below:

Column 1,
Lines 19, 57, 58, 60 and 63, delete "of ten" and insert -- often --

Column 4,
Lines 1, 4 and 54, delete "devises" and insert -- clevises --

Column 6,
Line 19, delete "of ten" and insert -- often --

Column 14,
Line 47, after "106' C" insert -- , --
Line 51, delete "devises" and insert -- clevises --

Column 15,
Line 14, delete "devises" and insert -- clevises --

Column 16,
Line 1, delete "116' A" and insert -- 116'" A --

Column 17,
Line 59, delete "115" C and 116' C, and 115' D" and insert -- 115'" C and 116'" C, and 115'" D --

Column 23,
Line 49, delete "a rejoined", insert -- are rejoined --

Signed and Sealed this

Twenty-fourth Day of February, 2004

JON W. DUDAS
*Acting Director of the United States Patent and Trademark Office*